(12) United States Patent
Liang et al.

(10) Patent No.: US 8,604,019 B2
(45) Date of Patent: Dec. 10, 2013

(54) COMPOUNDS FOR THE TREATMENT AND PROPHYLAXIS OF RESPIRATORY SYNCYTIAL VIRUS DISEASE

(71) Applicant: Hoffman-La Roche Inc., Nutley, NJ (US)

(72) Inventors: Chungen Liang, Shanghai (CN); Lisha Wang, Shanghai (CN); Hongying Yun, Shanghai (CN); Xiufang Zheng, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/648,550

(22) Filed: Oct. 10, 2012

(65) Prior Publication Data

US 2013/0090328 A1 Apr. 11, 2013

(30) Foreign Application Priority Data

Oct. 11, 2011 (WO) ................ PCT/CN2011/080627

(51) Int. Cl.
*A61K 31/553* (2006.01)
(52) U.S. Cl.
USPC .................................... 514/211.09
(58) Field of Classification Search
USPC .................................... 514/211.09
See application file for complete search history.

(56) References Cited

U.S. PATENT DOCUMENTS

2002/0099208 A1  7/2002  Yu et al.

FOREIGN PATENT DOCUMENTS

WO    2005/061513    7/2005

OTHER PUBLICATIONS

Intl Search Report for PCT/EP2012/069813 dated Jan. 25, 2013.
Chapman et al., *Antimicrobial Agents and Chemotherapy* 51(9):3346-3353 ( 2007).

*Primary Examiner* — Brandon Fetterolf
*Assistant Examiner* — Christopher R Stone

(57) ABSTRACT

The invention relates to the compounds of formula (I):

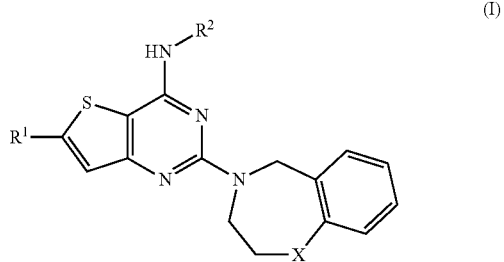

and pharmaceutically acceptable salts thereof, wherein $R^1$, $R^2$ and X are as defined in the description and claims, which are useful for the treatment or prophylaxis of RSV infection.

20 Claims, No Drawings

COMPOUNDS FOR THE TREATMENT AND PROPHYLAXIS OF RESPIRATORY SYNCYTIAL VIRUS DISEASE

PRIORITY TO RELATED APPLICATION(S)

This application claims the benefit of International Patent Application No. PCT/CN2011/080627, filed Oct. 11, 2011, which is hereby incorporated by reference in its entirety.

BACKGROUND OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and older children, RSV infection is mainly associated with upper respiratory track symptoms. Severe case of RSV infection often leads to bronchiolitis and pneumonia, which requires hospitalization. High-risk factors for lower respiratory tract infections include premature birth, congenital heart disease, chronic pulmonary disease, and immuno-compromised conditions. A severe infection at young age may lead to recurrent wheezing and asthma. For the elderly, RSV-related mortality rate becomes higher with advancing age.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophylaxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 April 25, Epub ahead of print).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor RSV-604 in stem cell transplantation patients by February 2010 (www.clinicaltrials.gov), but has not released the final results. Most of other small molecules were put on hold for various reasons.

RNAi therapeutics against RSV have also been thoroughly studied. ALN-RSV01 (Alnylam Pharmaceuticals, MA, USA) is an siRNA targeting on RSV gene. A nasal spray administered for two days before and for three days after RSV inoculation decreased infection rate among adult volunteers (DeVincenzo J. et al, Proc Natl Acad Sci USA. 2010 May 11; 107(19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4):531-8). Additional Phase IIb clinical trials in similar patient population for ALN-RSV01 are on-going (www.clinicaltrials.gov). Nevertheless, safe and effective treatment for RSV disease is needed urgently.

SUMMARY OF THE INVENTION

The invention relates to compounds which are respiratory syncytial virus (RSV) inhibitors, their manufacture, pharmaceutical compositions containing them, and their use in the treatment or prophylaxis of RSV infection. The invention relates in particular to the compounds of formula (I):

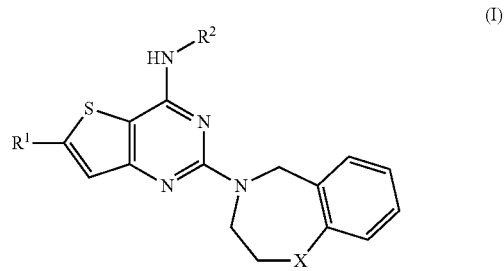

and pharmaceutically acceptable salts thereof, wherein $R^1$, $R^2$ and X are as defined in the detailed description and claims. It has been found that the compounds of formula I belong to a new chemical class of RSV inhibitors for the treatment or prophylaxis of RSV infection. The compounds of formula I are therefore useful in the treatment or prophylaxis of RSV disease.

DETAILED DESCRIPTION OF THE INVENTION

As used herein, the term "$C_{1-6}$alkyl" alone or in combination signifies a saturated, linear- or branched chain alkyl group containing 1 to 6 carbon atoms. In preferred embodiments the $C_{1-6}$alkyl contains 1 to 4 carbon atoms, for example methyl, ethyl, propyl, isopropyl, 1-butyl, 2-butyl, tert-butyl and the like. Preferred "$C_{1-6}$alkyl" groups are methyl, ethyl, isopropyl, and tert-butyl.

As used herein, the term "—$(CH_2)_{0-6}$—" signifies a chemical link, hydrogen, or a saturated, linear alkyl chain containing 1 to 6 carbon atoms. In preferred embodiments, the —$(CH_2)_{0-6}$— is hydrogen or a linear alkyl chain containing 1 to 4 carbon atoms.

As used herein, the term "—$(CH_2)_{1-6}$—" signifies a saturated, linear alkyl chain containing 1 to 6 carbon atoms. In preferred embodiments, the —$(CH_2)_{1-6}$— contains 1 to 4 carbon atoms.

As used herein, the term "—$(CH_2)_{2-6}$—" signifies a saturated, linear alkyl chain containing from 2 to 6 carbon atoms. In preferred embodiments, the —$(CH_2)_{2-6}$— contains 2 to 4 carbon atoms.

The term "halogen" means fluorine, chlorine, bromine or iodine. Halogen is preferably fluorine or chlorine, and more preferably fluorine.

The term "amino", alone or in combination, refers to a primary (—$NH_2$), secondary (—NH—) or tertiary amino

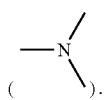

The term "oxetanyl" alone or in combination refers to the group

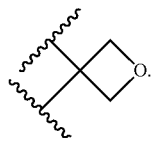 [SMILES: *C1(*)COC1]

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, in reference to a particular group or molecule, the term "substituted" refers to the fact that at least one of the hydrogen atoms of that group or molecule is replaced by some other substituent.

Unless otherwise indicated, the term "a compound of the formula" or "a compound of formula" or "compounds of the formula" or "compounds of formula" refers to any compound selected from the genus of compounds as defined by the formula.

In detail, the invention relates in particular to the compounds of formula (I):

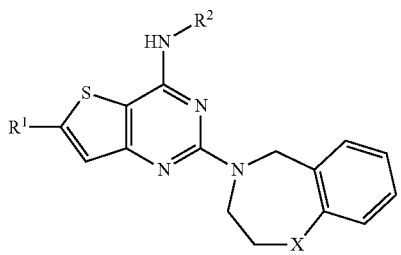

wherein
R$^1$ is hydrogen or C$_{1-6}$alkyl;
R$^2$ is (1) amino(CH$_2$)$_{2-6}$; (2) amino(CH$_2$)$_{1-6}$difluoromethyl (CH$_2$)$_{1-6}$; (3) amino(CH$_2$)$_{1-6}$fluoromethyl(CH$_2$)$_{1-6}$; (4) amino(CH$_2$)$_{0-6}$oxetanyl(CH$_2$)$_{1-6}$; (5) amino(CH$_2$)$_{1-6}$oxetanyl(CH$_2$)$_{0-6}$; or (6) pyrrolidin-3-yl, unsubstituted or 4-substituted by halogen;
X is —O—, —S—, —S(=O)—, —S(O$_2$)—, —CH$_2$—, —CF$_2$— or —NH—;
and pharmaceutically acceptable salt and stereoisomers thereof.

The compounds according to formula I do not include those in which the sp$^a$ hybrid carbon atom is disubstituted by two nitrogen atoms, or one nitrogen atom and one oxygen atom simultaneously.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

Compounds of the general formula (I) which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

In more particular embodiments, the present invention relates to a compound of formula (I) or a pharmaceutically acceptable salt thereof, wherein:
R$^1$ is hydrogen or methyl;
R$^2$ is

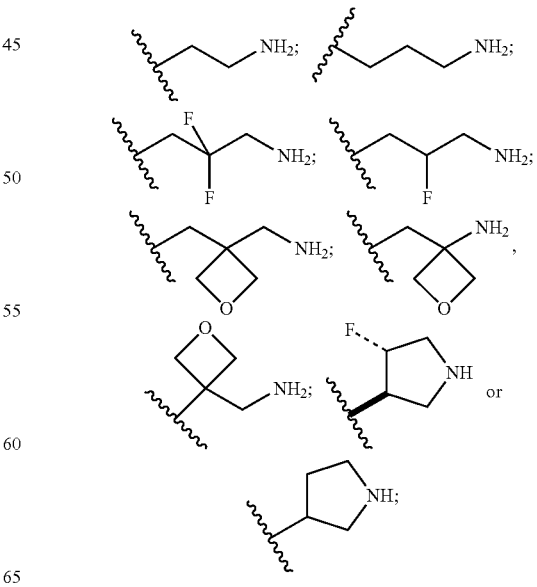

and

X is —O—, —S—, —S(=O)—, —S(O₂)—, —CH₂—, —CF₂— or —NH—.

In further embodiments, the present invention relates to a compound of formula (I) or a pharmaceutically acceptable salt thereof, wherein X is —S—, —S(=O)— or —S(O₂)—; and the remaining substituents are as defined in any of the above embodiments.

In other more specific embodiments, the present invention relates to a compound of formula (I) or a pharmaceutically acceptable salt thereof, wherein X is —S(=O)—; and the remaining substituents are as defined in any of the above embodiments.

In further particular embodiments, the present invention relates to a compound of formula (I) or a pharmaceutically acceptable salt thereof, wherein X is —S(O₂)—; and the remaining substituents are as defined in any of the above embodiments.

In other particular embodiments, the present invention relates to a compound of formula (I) or a pharmaceutically acceptable salt thereof, wherein:
  R¹ is hydrogen or methyl; and
  R² is aminopropyl; aminomethyldifluoromethylmethyl; aminomethyloxetanyl or aminooxetanylmethyl, and X is —S(O₂)—.

In particular embodiments, the present invention relates to a compound of formula (I) or a pharmaceutically acceptable salt thereof, selected from the group consisting of: N-[2-(1,1-dioxido-2,3-dihydro-1,4-benzothiazepin-4(5H)-yl)thieno[3,2-d]pyrimidin-4-yl]-2,2-difluoropropane-1,3-diamine; N-[2-(1-oxido-2,3-dihydro-1,4-benzothiazepin-4(5H)-yl)thieno[3,2-d]pyrimidin-4-yl]propane-1,3-diamine; N-[2-(2,3-dihydro-1,4-benzothiazepin-4(5H)-yl)thieno[3,2-d]pyrimidin-4-yl]propane-1,3-diamine; N-[2-(2,3-dihydro-1,4-benzothiazepin-4(5H)-yl)-6-methylthieno[3,2-d]pyrimidin-4-yl]propane-1,3-diamine; N-[2-(1,1-dioxido-2,3-dihydro-1,4-benzothiazepin-4(5H)-yl)-6-methylthieno[3,2-d]pyrimidin-4-yl]propane-1,3-diamine; N-[2-(1,1-dioxido-2,3-dihydro-1,4-benzothiazepin-4(5H)-yl)thieno[3,2-d]pyrimidin-4-yl]propane-1,3-diamine; N-[(3-aminooxetan-3-yl)methyl]-2-(1,1-dioxido-2,3-dihydro-1,4-benzothiazepin-4(5H)-yl)thieno[3,2-d]pyrimidin-4-amine; N-[3-(aminomethyl)oxetan-3-yl]-2-(1,1-dioxido-2,3-dihydro-1,4-benzothiazepin-4(5H)-yl)thieno[3,2-d]pyrimidin-4-amine; N-[(3-aminooxetan-3-yl)methyl]-2-[(1R)-1-oxido-2,3-dihydro-1,4-benzothiazepin-4(5H)-yl]thieno[3,2-d]pyrimidin-4-amine; N-[(3-aminooxetan-3-yl)methyl]-2-[(1S)-1-oxido-2,3-dihydro-1,4-benzothiazepin-4(5H)-yl]thieno[3,2-d]pyrimidin-4-amine; N-[(3-aminooxetan-3-yl)methyl]-6-methyl-2-(1-oxido-2,3-dihydro-1,4-benzothiazepin-4(5H)-yl)thieno[3,2-d]pyrimidin-4-amine; 2-fluoro-N-[6-methyl-2-(1-oxido-2,3-dihydro-1,4-benzothiazepin-4(5H)-yl)thieno[3,2-d]pyrimidin-4-yl]propane-1,3-diamine; N-[6-methyl-2-(1-oxido-2,3-dihydro-1,4-benzothiazepin-4(5H)-yl)thieno[3,2-d]pyrimidin-4-yl]ethane-1,2-diamine; N-{[3-(aminomethyl)oxetan-3-yl]methyl}-6-methyl-2-(1-oxido-2,3-dihydro-1,4-benzothiazepin-4(5H)-yl)thieno[3,2-d]pyrimidin-4-amine; N-[6-methyl-2-(1-oxido-2,3-dihydro-1,4-benzothiazepin-4(5H)-yl)thieno[3,2-d]pyrimidin-4-yl]propane-1,3-diamine; N-[trans-(±)-4-fluoropyrrolidin-3-yl]-6-methyl-2-(1-oxido-2,3-dihydro-1,4-benzothiazepin-4(5H)-yl)thieno[3,2-d]pyrimidin-4-amine; 6-methyl-2-(1-oxido-2,3-dihydro-1,4-benzothiazepin-4(5H)-yl)-N-(pyrrolidin-3-yl)thieno[3,2-d]pyrimidin-4-amine; N-[6-methyl-2-(1,2,3,5-tetrahydro-4H-1,4-benzodiazepin-4-yl)thieno[3,2-d]pyrimidin-4-yl]propane-1,3-diamine; N-[2-(1,2,3,5-tetrahydro-4H-1,4-benzodiazepin-4-yl)thieno[3,2-d]pyrimidin-4-yl]propane-1,3-diamine; N-[2-(2,3-dihydro-1,4-benzoxazepin-4(5H)-yl)thieno[3,2-d]pyrimidin-4-yl]propane-1,3-diamine; N-[2-(5,5-difluoro-1,3,4,5-tetrahydro-2H-2-benzazepin-2-yl)thieno[3,2-d]pyrimidin-4-yl]propane-1,3-diamine; N-{[3-(aminomethyl)oxetan-3-yl]methyl}-2-(5,5-difluoro-1,3,4,5-tetrahydro-2H-2-benzazepin-2-yl)thieno[3,2-d]pyrimidin-4-amine; N-[2-(1,3,4,5-tetrahydro-2H-2-benzazepin-2-yl)thieno[3,2-d]pyrimidin-4-yl]propane-1,3-diamine; N-[2-(2,3-dihydro-1,4-benzoxazepin-4(5H)-yl)-6-methylthieno[3,2-d]pyrimidin-4-yl]propane-1,3-diamine; N-[2-(5,5-difluoro-1,3,4,5-tetrahydro-2H-2-benzazepin-2-yl)-6-methylthieno[3,2-d]pyrimidin-4-yl]propane-1,3-diamine; and N-[6-methyl-2-(1,3,4,5-tetrahydro-2H-2-benzazepin-2-yl)thieno[3,2-d]pyrimidin-4-yl]propane-1,3-diamine.

The compounds of the present invention can be prepared by any conventional means. Suitable processes for synthesizing these compounds as well as their starting materials are provided in the schemes below and in the examples. All substituents, in particular, R¹, R² and X are as defined in the Schemes unless otherwise indicated. Furthermore, and unless explicitly otherwise stated, all reactions, reaction conditions, abbreviations and symbols have the meanings well known to a person of ordinary skill in organic chemistry.

| | Abbreviations |
|---|---|
| RSV: | Respiratory Syncytial Virus |
| DMSO-d6: | deuterated dimethylsulfoxide |
| FBS: | fetal bovine serum |
| LongStrain: | an A subtype RSV strain obtained from ATCC with catalog number VR-26 |
| g: | gram |
| EC₅₀: | the concentration of a compound where 50% of its maximal protection effect against viral induced CPE is observed |
| HPLC: | high performance liquid chromatography |
| Hz: | Hertz |
| CHLOROFORM-d: | deuterated chloroform |
| METHANOL-d₄: | deuterated methanol |
| mg: | milligram |
| MHz: | megahertz |
| L: | liter |
| mL: | milliliter |
| mmol: | millimole |
| obsd. | observed |
| µm: | micrometer |
| M: | moles per liter |
| µM: | micromoles per liter |
| N: | normality |
| mm: | millimeter |
| min: | minute |
| LC/MS: | Liquid chromatography/mass spectrometry |
| MS (ESI): | mass spectroscopy (electron spray ionization) |
| NMR: | nuclear magnetic resonance |

General synthetic route for formulas Ia (Scheme 1):

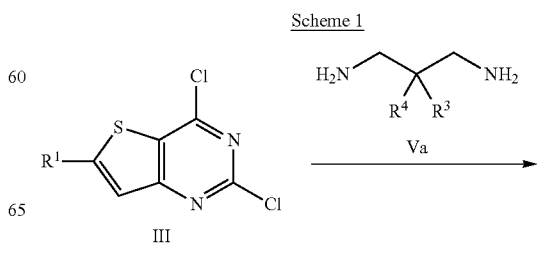

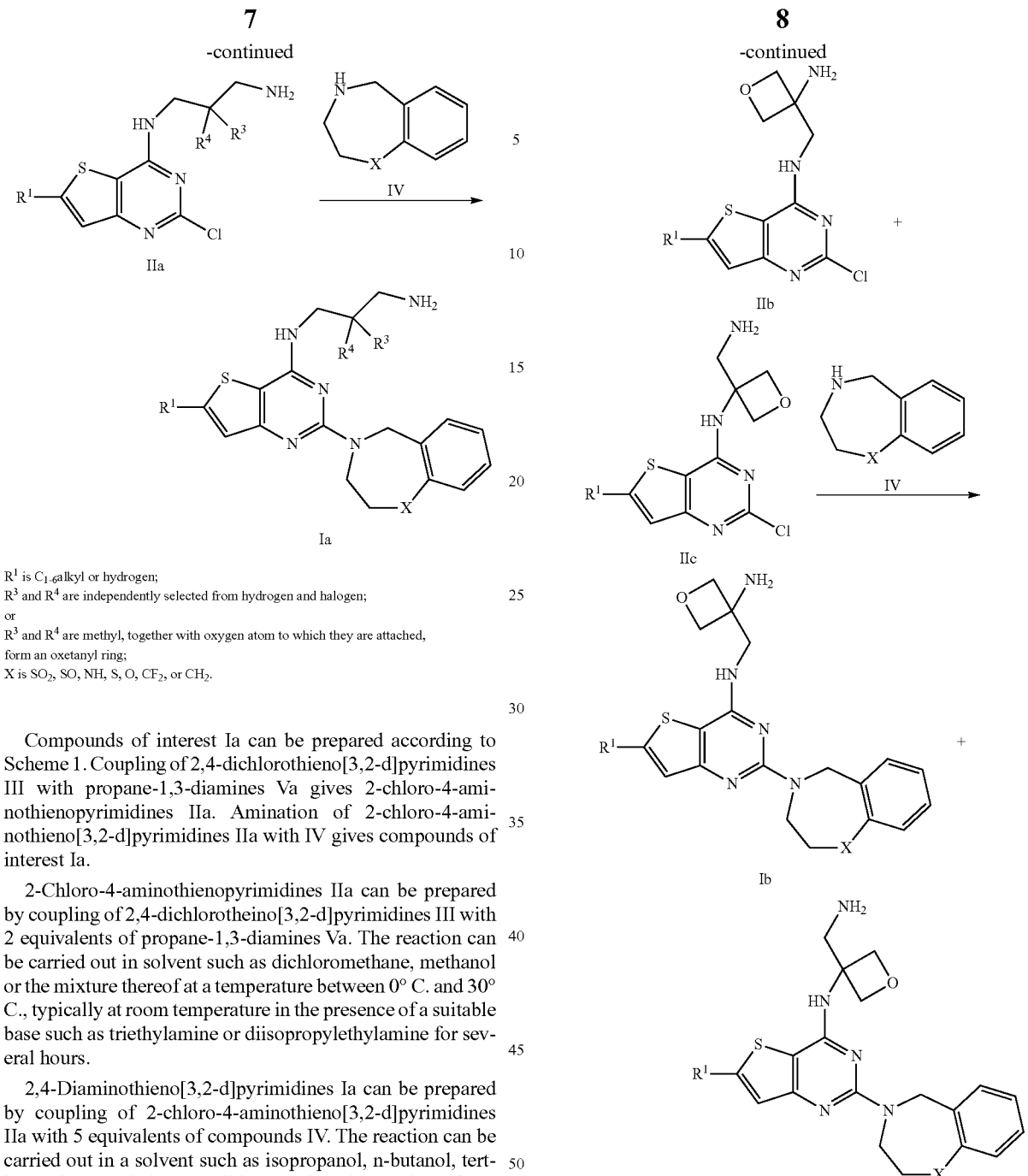

$R^1$ is $C_{1-6}$alkyl or hydrogen;
$R^3$ and $R^4$ are independently selected from hydrogen and halogen;
or
$R^3$ and $R^4$ are methyl, together with oxygen atom to which they are attached, form an oxetanyl ring;
X is $SO_2$, SO, NH, S, O, $CF_2$, or $CH_2$.

Compounds of interest Ia can be prepared according to Scheme 1. Coupling of 2,4-dichlorothieno[3,2-d]pyrimidines III with propane-1,3-diamines Va gives 2-chloro-4-aminothienopyrimidines IIa. Amination of 2-chloro-4-aminothieno[3,2-d]pyrimidines IIa with IV gives compounds of interest Ia.

2-Chloro-4-aminothienopyrimidines IIa can be prepared by coupling of 2,4-dichlorotheino[3,2-d]pyrimidines III with 2 equivalents of propane-1,3-diamines Va. The reaction can be carried out in solvent such as dichloromethane, methanol or the mixture thereof at a temperature between 0° C. and 30° C., typically at room temperature in the presence of a suitable base such as triethylamine or diisopropylethylamine for several hours.

2,4-Diaminothieno[3,2-d]pyrimidines Ia can be prepared by coupling of 2-chloro-4-aminothieno[3,2-d]pyrimidines IIa with 5 equivalents of compounds IV. The reaction can be carried out in a solvent such as isopropanol, n-butanol, tert-butanol, N-methyl-2-pyrrolidone or the mixture thereof at a temperature between 120° C. and 180° C., typically at 160° C. under microwave irradiation for several hours.

General Synthetic Route for Formulas Ib and Ic (Scheme 2)

Scheme 2

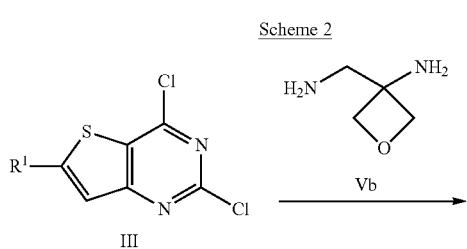

$R^1$ is $C_{1-6}$alkyl or hydrogen;
X is SO, $SO_2$, NH, S, O, $CF_2$, or $CH_2$.

Compounds of interest Ib and Ic can be prepared according to Scheme 2. Coupling of 2,4-dicholorothieno[3,2-d]pyrimidine III with Vb gives a mixture of 2-chloro-4-aminothieno[3,2-d]pyrimidines IIb and IIe. Reaction of compounds IV with IIb and IIc gives compounds of interest Ib and Ic.

2-Chloro-4-aminothieno[3,2-d]pyrimidines IIb and IIc can be prepared by coupling of 2,4-dichlorotheino[3,2-d]pyrimidine III with 2 equivalents of Vb. The reaction can be carried out in a solvent such as dichloromethane, methanol or the mixture thereof at a temperature between 0° C. and 30° C., typically at room temperature in the presence of a suitable base such as triethylamine, diisopropylethylamine for several hours.

Thieno[3,2-d]pyrimidines Ib and Ic can be prepared by coupling of 2-chloro-4-aminothieno[3,2-d]pyrimidines IIb and IIc with 5 equivalents of IV. The reaction can be carried out in a solvent such as isopropanol, n-butanol, tert-butanol, N-methyl-2-pyrrolidone or the mixture thereof at a temperature between 120° C. and 180° C., typically at 160° C. under microwave irradiation for several hours.

General Synthetic Route for Formulas Id (Scheme 3)

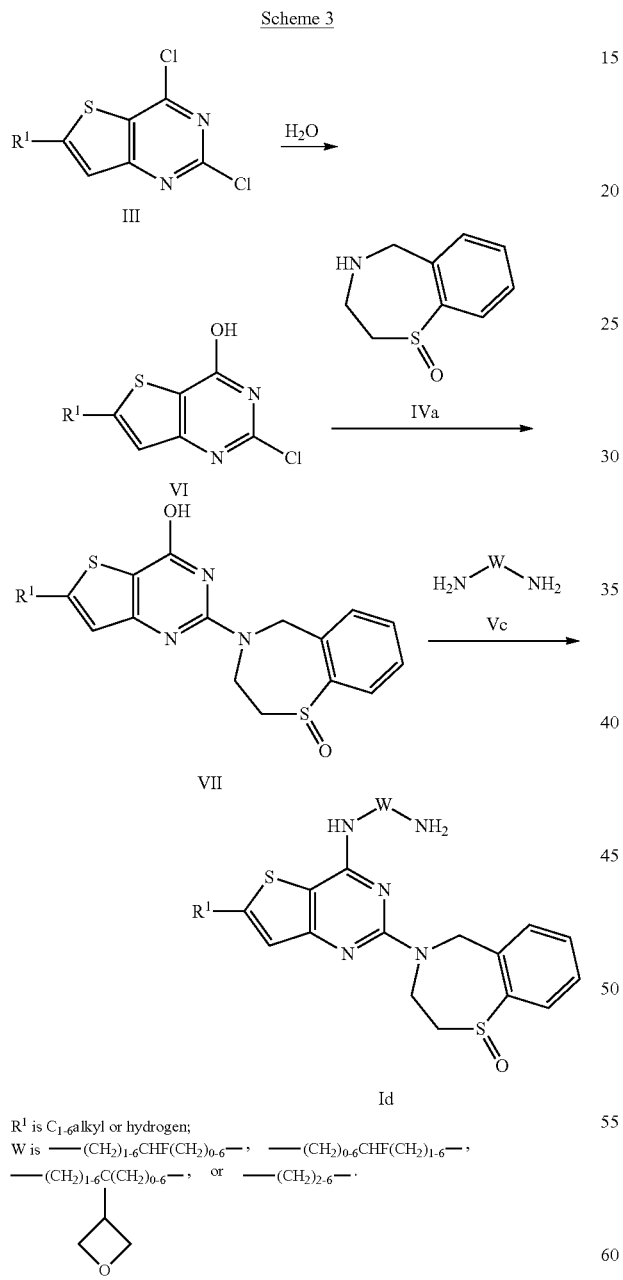

Compounds of interest Id can be prepared according to Scheme 3. Hydrolysis of 2,4-dichlorothieno[3,2-d]pyrimidine III gives 2-chloro-4-hydroxylthieno[3,2-d]pyrimidine VI, followed by coupling with IVa to give VII. Coupling of VII with Vc gives compounds of interest Id.

VI can be prepared by hydrolysis of III. The reaction can be achieved by stirring of III with aqueous NaOH in THF at room temperature for several hours.

VII can be prepared by amination of VI with 2 equivalents of IVa. The reaction can be carried out in a solvent such as isopropanol, n-butanol, tert-butanol, N-methyl-2-pyrrolidone or the mixture thereof at a temperature between 120° C. and 180° C., typically at 160° C. under microwave irradiation for several hours.

Compounds of interest Id can be prepared by coupling of VII with Vc. The reaction can be carried out in the presence of a suitable base such as 1,8-diazabicyclo[5.4.0]undec-7-ene with a suitable phosphine ligand such as benzotriazol-1-yloxytris(dimethylamino)-phosphonium hexafluorophosphate, in a suitable solvent such as N,N-dimethylformamide at room temperature for several hours.

General Synthetic Route for Formulas Ie (Scheme 4)

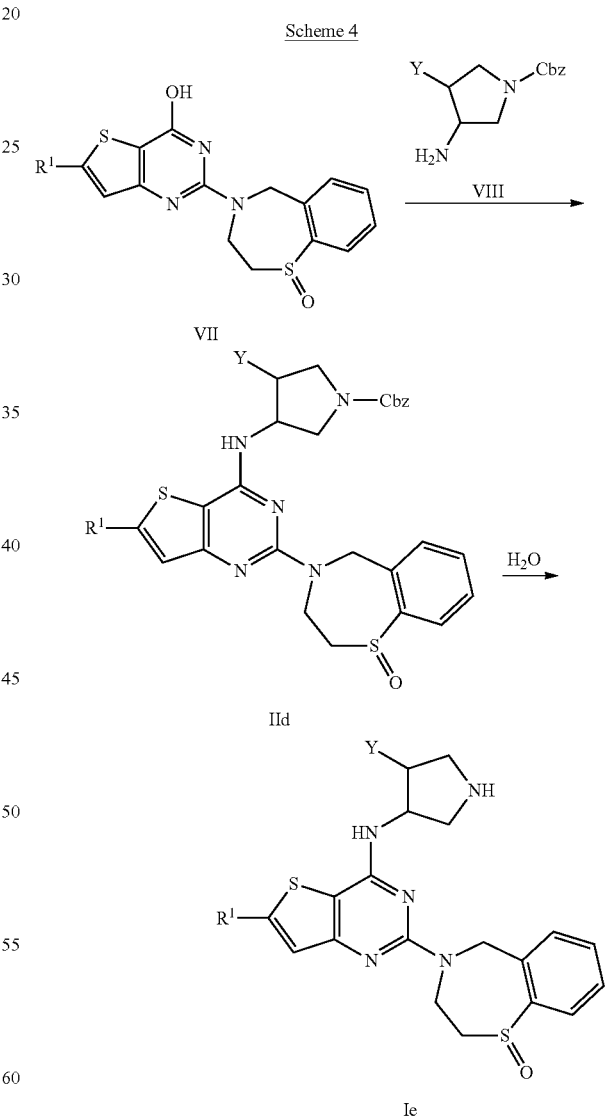

$R^1$ is hydrogen or $C_{1-6}$alkyl;
Y is hydrogen or halogen.

Compounds of interest Ie can be prepared according to Scheme 4. Coupling of VII with amines VIII gives 2,4-diaminothienopyrimidines IId, followed by cleavage of benzoxycarbonyl to afford compounds of interest Ie.

2,4-diaminothienopyrimidines IId can be prepared by coupling of VII with trans-3-amino-4-fluoropyrrolidine-1-carboxylic acid benzyl ester or trans-3-aminopyrrolidine-1-carboxylic acid benzyl ester respectively. The reaction can be carried out in the presence of benzotriazol-1-yloxytris(dimethylamino)phosphonium hexafluorophosphate, with a suitable base such as 1,8-diazabicyclo[5.4.0]undec-7-ene or triethylamine, in a suitable solvent such as N,N-dimethylformamide or acetonitrile at room temperature overnight.

Compounds of interest Ie can be prepared by cleavage of benzyl carbamates IId. The conversion can be achieved by refluxing a solution of IId in methanol in the presence of a strong base such as 40% aqueous KOH for several hours.

This invention also relates to a process for the preparation of a compound of formula (I) comprising one of the following steps:

(a) the reaction of a compound of formula (A)

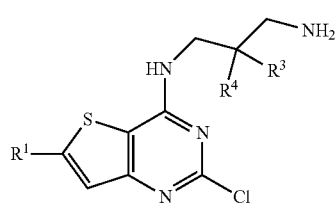

in the presence of

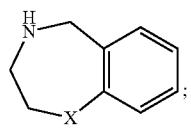

(b) the reaction of a compound of formula (B)

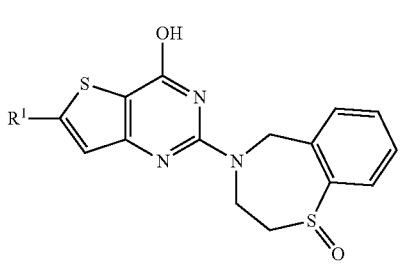

in the presence of

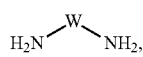

a base and a ligand;

(c) the reaction of a compound of formula (C)

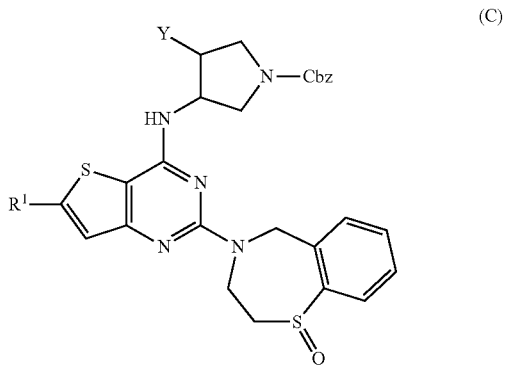

in the presence of a base;
wherein $R^1$, $R^3$, $R^4$, W, X and Y are defined as in the Schemes above unless otherwise indicated.

In step (b), the base can be for example 1,8-diazabicyclo[5.4.0]undec-7-ene; the ligand can be for example benzotriazol-1-yloxytris(dimethylamino)-phosphonium hexafluorophosphate.

In step (c), the base can be for example potassium hydroxide.

The invention also relates to a compound of formula (I) for use as therapeutically active substance.

The invention relates to a compound of formula (I) for use as a medicament.

The invention also relates to a pharmaceutical composition comprising a compound of formula (I) and a therapeutically inert carrier.

The invention relates in particular to the use of a compound of formula (I) for the preparation of a medicament for the treatment or prophylaxis of respiratory syncytial virus infection.

Said medicaments, e.g. in the form of pharmaceutical preparations, can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. For example, lactose, corn starch or derivatives thereof, talc, stearic acids or its salts and the like can be used, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 25-200 mg/kg, and can be taken singly or distributed over several administrations.

A compound of formula (I) when manufactured according to the above process is also an object of the invention.

This invention relates to the use of a compound of formula (I) for the manufacture of a medicament for treatment or prophylaxis of RSV infection.

The invention further relates to a method for the treatment or prophylaxis of respiratory syncytial virus infection, which method comprises administering an effective amount of a compound of formula (I).

The invention is illustrated by the following examples which have no limiting character. Unless explicitly otherwise stated, all reactions, reaction conditions, abbreviations and symbols have the meanings well known to a person of ordinary skill in organic chemistry.

EXAMPLES

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes): Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

Intermediate 1

2,3,4,5-Tetrahydro-1,4-benzothiazepine

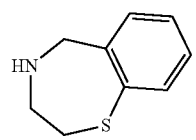

Step 1. Preparation of Methyl 2-sulfanylbenzoate

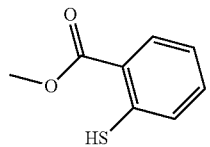

To a cooled solution of concentrated sulfuric acid (72 g) in methanol (1.5 L) at 0° C., was added 2-sulfanylbenzoic acid (300 g, 1.95 mol) in portions under argon atmosphere. After being refluxed with stirring for 18 hours, the reaction mixture was concentrated in vacuo. The residue was diluted with water (800 mL), basified with a saturated aqueous solution of sodium bicarbonate to about pH 7, and extracted with dichloromethane (600 mL×3). The combined organic layers were washed with brine (800 mL), dried over sodium sulfate, filtered and concentrated in vacuo to afford 300 g of methyl 2-sulfanylbenzoate (yield was 90%) as a light yellow oil, which was used for the next step without further purification.

Step 2. Preparation of
3,4-Dihydro-1,4-benzothiazepin-5(2H)-one

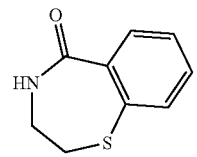 [SMILES: O=C1NCCSc2ccccc21]

To a cooled solution of methyl 2-sulfanylbenzoate (200 g, 1.19 mol) in tetrahydrofuran and N,N-dimethylformamide (2 L, V/V=1/1) was added 2-chloroethanamine hydrochloride (138 g, 1.19 mol) at 0° C. followed by sodium hydride (143 g, 3.57 mol, 60% in mineral oil) in portions. After being stirred at room temperature overnight, the reaction mixture was poured into ice-water and extracted with ethyl acetate (900 mL×4). The organic layers were combined, washed with brine (900 mL×3), dried over sodium sulfate and concentrated in vacuo. The residue was stirred in a mixture solution of ethyl acetate and petroleum ether (300 mL, V/V=1/1) for 1 hour. The solid was collected by filtration and dried in vacuo to afford 100 g of 3,4-dihydro-1,4-benzothiazepin-5(2H)-one (yield was 47%).

Step 3. Preparation of
2,3,4,5-Tetrahydro-1,4-benzothiazepine

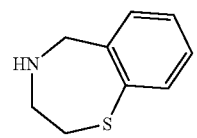 [SMILES: c1ccc2c(c1)CNCCS2]

To a bottle containing a cooled suspension of lithium aluminum hydride (44 g, 1.17 mol) in dry tetrahydrofuran (1.5 L) was added 3,4-dihydro-1,4-benzothiazepin-5(2H)-one (150 g, 0.84 mol) in portions at 0° C. After being refluxed for 18 hours, the reaction mixture was cooled to 0° C., followed by addition of water (25 mL) dropwise. The reaction mixture was then filtered through a pad of celite and washed with dichloromethane. The filtrate was dried over sodium sulfate and evaporated in vacuo to afford 125 g of 2,3,4,5-tetrahydro-1,4-benzothiazepine (yield was 90%), which was used for the next step without further purification.

Intermediate 2

2,3,4,5-Tetrahydro-1,4-benzothiazepine-1,1-dioxide

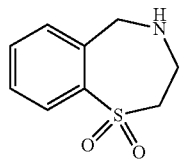 [SMILES: O=S1(=O)CCNCc2ccccc21]

Step 1. Preparation of 1-(2,3-Dihydro-1,4-benzothiazepin-4(5H)-yl)ethanone

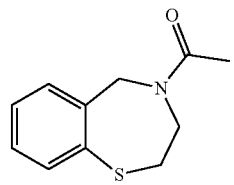

To a solution of 2,3,4,5-tetrahydro-1,4-benzothiazepine (5 g, 30.3 mmol) in dry dichloromethane (100 mL) was added triethylamine (5.06 mL, 36.3 mmol) at room temperature, followed by the addition of acetic anhydride (3.43 mL, 36.3 mmol) dropwise at 0° C. under nitrogen. The resulting solution was stirred for 1 hour whilst allowing the temperature to rise slowly to room temperature. The mixture was washed with brine (50 mL×2), dried over sodium sulfate, filtered and concentrated in vacuo to afford 6.28 g of product as yellow oil, which was used for next step without further purification.

Step 2. Preparation of 1-(1,1-Dioxido-2,3-dihydro-1,4-benzothiazepin-4(5H)-yl)ethanone

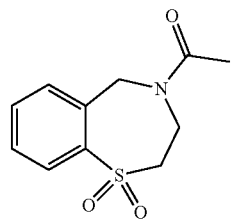 [SMILES: CC(=O)N1CCS(=O)(=O)c2ccccc2C1]

To a cooled solution of 1-(2,3-dihydro-1,4-benzothiazepin-4(5H)-yl)ethanone (6.27 g, 30.2 mmol) in dichloromethane (100 mL) was added a suspension of 3-chloroperoxybenzoic acid (20.9 g, 90.8 mmol, 75% purity) in dichloromethane (50 mL) at 10° C. After the addition, the resulting mixture was stirred for 1 hour whilst allowing the temperature to rise slowly to room temperature. The mixture was washed with a saturated aqueous solution of sodium carbonate (100 mL×2), a saturated aqueous solution of sodium sulfite (100 mL×2) and brine (100 mL). The organic layer was dried over sodium sulfate, filtered and concentrated in vacuo. The residue was stirred in diethyl ether (50 mL) and the solid was collected by filtration and dried in vacuo to afford 6 g of 1-(1,1-dioxido-2,3-dihydro-1,4-benzothiazepin-4(5H)-yl)ethanone as a white powder.

Step 3. Preparation of 2,3,4,5-Tetrahydro-1,4-benzothiazepine 1,1-dioxide

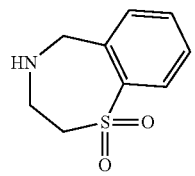 [SMILES: O=S1(=O)CCNCc2ccccc21]

To a solution of 1-(1,1-dioxido-2,3-dihydro-1,4-benzothiazepin-4(5H)-yl)ethanone (240 g, 1.0 mol) in ethanol (1.0 L) was added sodium hydroxide (200 g, 5.0 mol) and water (700 mL). The mixture was refluxed overnight and then concentrated in vacuo. The residue was extracted by ethyl acetate (1500 mL×4). The combined organic layers were extracted by hydrochloric acid (2000 mL, 3 N). The acidic aqueous layer was washed with ethyl acetate (1500 mL×2), then basified with a saturated aqueous solution of sodium bicarbonate to pH>7, and extracted with ethyl acetate (1500 mL×4). The combined organic layers were dried over sodium sulfate, filtered and concentrated in vacuo to afford 151 g of 2,3,4,5-tetrahydro-1,4-benzothiazepine 1,1-dioxide (yield was 76%), MS obsd. (ESI$^+$) [(M+H)$^+$] 198, $^1$H NMR (400 MHz, DMSO-d$_6$) δ ppm 7.89 (dd, J=1.2, 7.6 Hz, 1H), 7.56 (t, J=7.6 Hz, 1H), 7.47 (t, J=7.6 Hz, 1H), 7.42 (d, J=7.6 Hz, 1H), 4.04 (s, 2H), 3.32-3.30 (m, 2H), 3.30-3.25 (m, 2H), 2.64 (s, 1H).

Intermediate 3

2,3,4,5-Tetrahydro-1,4-benzothiazepine 1-oxide

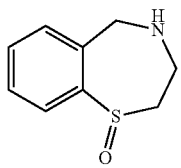 [SMILES: O=S1CCNCc2ccccc21]

Step 1. Preparation of 1-(1-Oxido-2,3-dihydro-1,4-benzothiazepin-4(5H)-yl)ethanone

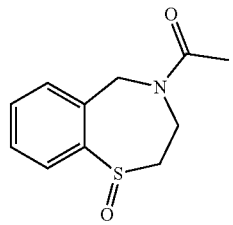

To a cooled solution of 1-(2,3-dihydro-1,4-benzothiazepin-4(5H)-yl)ethanone (70 g, 0.33 mol) in dichloromethane (700 mL) was added a solution of 3-chloroperoxybenzoic acid (67 g, 0.33 mol) in dichloromethane (800 mL) dropwise at 0° C. After the addition, the reaction was stirred at the same temperature for 15 minutes. The resulting reaction mixture was washed with a saturated aqueous solution of sodium carbonate (500 mL×2) and a saturated aqueous solution of sodium sulfite (500 mL×2). The combined aqueous layers were extracted with dichloromethane (200 mL×2), dried over sodium sulfate and concentrated in vacuo. The residue was purified by flash chromatography (eluting with 1-2% methanol in dichloromethane) to afford 57 g of the desired product (yield was 77%).

Step 2. Preparation of 2,3,4,5-Tetrahydro-1,4-benzothiazepine-1-oxide

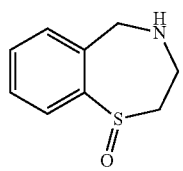 [SMILES: O=S1CCNCc2ccccc21]

Intermediate 3 was prepared in analogy to intermediate 2 by using 1-(1-oxido-2,3-dihydro-1,4-benzothiazepin-4(5H)-yl)ethanone (yield was 66%), MS obsd. (ESI$^+$) [(M+H)]181, $^1$H NMR (400 MHz, METHANOL-d4) δ ppm 7.72 (dd, J=1.6, 7.6 Hz, 1H), 7.52-7.48 (m, 2H), 7.33 (dd, J=1.6, 7.2 Hz, 1H), 4.21-4.11 (m, 1H), 3.82-3.80 (m, 1H), 3.62-3.50 (m, 2H), 3.22-3.19 (m, 2H).

Intermediate 4

5,5-Difluoro-2,3,4,5-tetrahydro-1H-benzazepine

Step 1. Preparation of 1-(5,5-Difluoro-1,3,4,5-tetrahydro-2H-2-benzazepin-2-yl)-2,2,2-trifluoroethanone

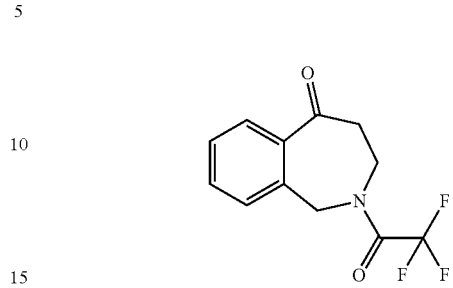

To a cooled solution of 1,2,3,4-tetrahydro-1-benzazepin-5-one hydrochloride (33.7 g, 0.17 mol) in dichloromethane (500 mL) at 0° C., was added triethylamine (52 g, 0.51 mol) dropwise followed by trifluoroacetic anhydride (36 g, 0.17 mmol). After being stirred at room temperature for 3 hours, the resulting mixture was diluted with water (300 mL). The aqueous layer was extracted with dichloromethane (500 mL). The combined organic layers were washed with a saturated aqueous solution of sodium bicarbonate (500 mL) and brine (500 mL), dried over sodium sulfate and concentrated in vacuo. The residue was purified by flash chromatography (eluting with 16% ethyl acetate in petroleum ether) to afford 40 g of the desired product (yield was 89%).

Step 2. Preparation of 1-(5,5-Difluoro-1,3,4,5-tetrahydro-2H-2-benzazepin-2-yl)-2,2,2-trifluoroethanone

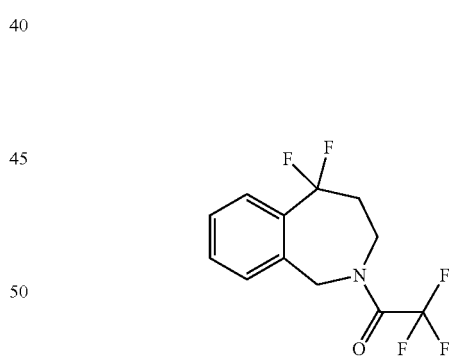

A solution of 2-(trifluoroacetyl)-1,2,3,4-tetrahydro-5H-2-benzazepin-5-one (40 g, 0.156 mol) in N,N-diethylaminosulfur trifluoride (104 g, 0.468 mol) was heated at 70° C. for 3 hours. The reaction mixture was poured into ice-water (600 mL) and extracted with dichloromethane (800 mL). The organic layer was washed with a saturated aqueous solution of sodium bicarbonate (500 mL) and brine (500 mL), dried over sodium sulfate, and concentrated in vacuo. The residue was purified by flash chromatography (eluting with 16% ethyl acetate in petroleum ether) to give 33 g of the desired product (yield was 76%).

Step 3. Preparation of
5,5-Difluoro-2,3,4,5-tetrahydro-1H-benzazepine

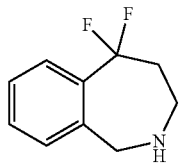 [SMILES: FC1(F)CCNCc2ccccc21]

To a cooled solution of 1-(5,5-difluoro-1,3,4,5-tetrahydro-2H-2-benzazepin-2-yl)-2,2,2-trifluoroethanone (33 g, 0.184 mmol) in methanol was added an ammonia methanol solution (300 mL, 7 M) at 0° C. After being stirred at 0° C. for 2 hours, the reaction mixture was concentrated in vacuo. The residue was purified by flash chromatography (eluting with 10~25% ethyl acetate in petroleum ether) to afford 18 g of the desired product as a purple oil (yield was 83.3%), MS obsd. (ESI+) [(M+H)+] 184, $^1$H NMR (400 MHz, CHLOROFORM-d) δ ppm 7.64-7.60 (m, 1H), 7.34-7.25 (m, 2H), 7.16-7.14 (m, 1H), 7.01 (s, 2H), 3.33-3.30 (m, 2H), 2.33-2.24 (m, 2H).

Intermediate 5 tert-Butyl [(3-aminooxetan-3-yl)methyl]carbamate

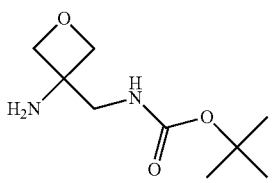

Step 1. Preparation of tert-Butyl{[3-(dibenzylamino)oxetan-3-yl]methyl}carbamate

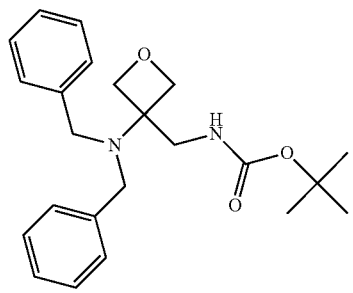 [SMILES: CC(C)(C)OC(=O)NCC1(N(Cc2ccccc2)Cc2ccccc2)COC1]

To a solution of 3-(aminomethyl)-N,N-dibenzyloxetan-3-amine (10.0 g, 33.97 mmol) in tetrahydrofuran (100 mL) was added an aqueous solution of sodium bicarbonate (8.6 g, 101.9 mmol dissolved in 50 mL of water) and a solution of di-tert-butyl dicarbonate (8.9 g, 40.76 mmol) in tetrahydrofuran (30 mL). The mixture was stirred at room temperature overnight, then concentrated in vacuo to remove most of the organic solvent, and the aqueous residue was extracted with dichloromethane (100 mL×3). The organic layers were combined, washed with brine (150 mL), dried over anhydrous sodium sulfate and concentrated in vacuo to afford 13.0 g of the crude product, which was used for the next step without any purification.

Step 2. Preparation of tert-Butyl
[(3-aminooxetan-3-yl)methyl]carbamate

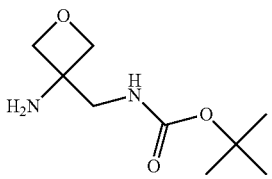

A mixture of tert-butyl {[3-(dibenzylamino)oxetan-3-yl]methyl}carbamate (13.0 g, crude), 20% palladium hydroxide on carbon (2.0 g) and trifluoroacetic acid (0.5 mL) in methanol (20 mL) was stirred overnight under hydrogen atmosphere (1 bar). After being basified with ammonia solution in methanol, the resulting mixture was filtered and concentrated in vacuo to afford 5.8 g of the crude product, which was used for the next step without any purification.

Intermediate 6

2-Fluoropropane-1,3-diamine

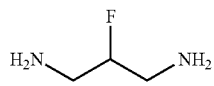

Step 1. Preparation of 2-Fluoropropanediamide

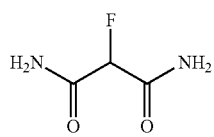

To a solution of 1,3-diethyl 2-difluoropropanedioate (25 g, 140.4 mmol) in methanol (100 mL) under a nitrogen atmosphere was added a solution of ammonia in methanol (80 mL, 7 N, 560 mmol). The resulting mixture was stirred at room temperature overnight and then concentrated in vacuo. The residue was triturated in petroleum ether to afford 16.3 g of 2-fluoropropanediamide as a white solid (yield was 97%). MS obsd. (ESI⁺) [(M+H)⁺] 121.

Step 2. Preparation of 2-Fluoropropane-1,3-diamine

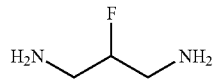

To a solution of 2-fluoropropanediamide (16.3 g, 136 mmol) in tetrahydrofuran (200 mL) was added a solution of boran-tetrahydrofuran complex (800 mL, 800 mmol, 1 M) in tetrahydrofuran. The reaction mixture was heated at 70° C. with stirring overnight, then cooled in an ice bath, stirred with methanol (100 mL) further for 30 minutes, and concentrated in vacuo. The residue was dissolved in methanol (100 mL) and the solution was concentrated in vacuo. To the residue was added water (10 mL), then potassium hydroxide was added with cooling until the aqueous solution was saturated. The mixture was extracted by diethyl ether (20 mL×2), and the combined organic layers was dried over potassium hydroxide and concentrated in vacuo to afford 7.5 g of 2-fluoropropane-1,3-diamine (yield was 60%). MS obsd. (ESI⁺) [(M+H)⁺] 93.

Intermediate 7

Oxetane-3,3-diyldimethanamine

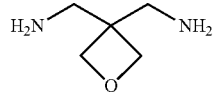

Step 1. Preparation of 3,3-Bis-azidomethyl-oxetane

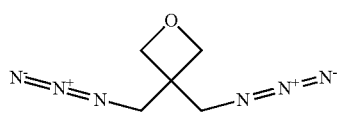 [SMILES: [N-]=[N+]=NCC1(CN=[N+]=[N-])COC1]

A mixture of 3,3-bis(bromomethyl)oxetane (25 g, 100 mmol) and sodium azide (14.3 g, 220 mmol) in water (65 ml) was added tetrabutylazanium bromide (1.61 g, 5 mmol). The reaction mixture was heated with stirring at 70° C. overnight. The reaction mixture was cooled to room temperature and extracted with dichloromethane (50 mL×3). The combined organic layers were washed with water, dried over sodium sulphate and concentrated in vacuo to afford 18.7 g of 3,3-bis-azidomethyl-oxetane as light yellow oil. The crude product was used for next step without further purification.

Step 2. Preparation of Oxetane-3,3-diyldimethanamine

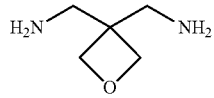

A solution of 3,3-bisazidomethyloxetane (18.7 g) in methanol (15 ml) was stirred in the presence of 10% palladium on carbon (1.8 g) under hydrogen atmosphere at room temperature for 5 hours. The reaction mixture was filtered and the filtrate was concentrated in vacuo to afford oxetane-3,3-diyldimethanamine (17 g) as a light yellow solid.

Intermediate 8 trans-(±)-Benzyl 3-amino-4-fluoroypyrrolidne-1-carobxylate

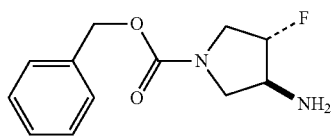 [SMILES: N[C@H]1CN(C(=O)OCc2ccccc2)C[C@@H]1F]

Step 1. Preparation of trans-(±)-Benzyl 3-azido-4-fluoroypyrrolidne-1-carobxylate

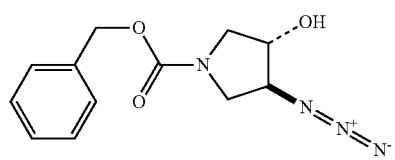 [SMILES: [N-]=[N+]=N[C@H]1CN(C(=O)OCc2ccccc2)C[C@@H]1O]

To a solution of benzyl-6-oxa-3-azabicyclo[3.1.0]hexane-3-carboxylate (2.5 g) in methanol (20 mL) was added water (5 mL), ammonium chloride (550 mg) and sodium azide (1.5 g). The resulting mixture was heated at 65° C. for 21 hours. The solids were removed by filtration and the filtrate was concentrated in vacuo. The residue was poured into 15% aqueous solution of sodium hydroxide (30 mL) and extracted with dichloromethane (50 mL). The organic layers were washed with brine, dried over magnesium sulfate and concentrated in vacuo to afford 2.7 g of trans-(±) benzyl-3-azido-4-hydroxy-pyrrolidne-1-carobxylate. MS obsd. (ESI⁺) [(M+H)⁺] 250.

Step 2. Preparation of trans-(±)-Benzyl 3-azido-4-fluoroypyrrolidne-1-carobxylate

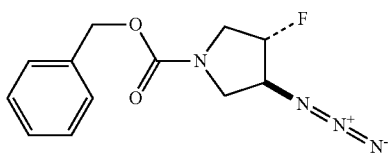 [SMILES: [N-]=[N+]=N[C@H]1CN(C(=O)OCc2ccccc2)C[C@@H]1F]

To a cooled solution of trans-(±) benzyl-3-azido-4-hydroxypyrrolidne-1-carobxylate (6.5 g) in dichloromethane (110 mL) was added diethylaminosulfur trifluoride (6.8 mL) at −78° C. The mixture was stirred at room temperature for 16 hours, and then concentrated in vacuo. The residue was dissolved in ethyl acetate (100 mL), and the solution was washed with a saturated sodium bicarbonate (100 mL) and brine (100 mL), dried over magnesium sulfate and concentrated in vacuo. The residue was purified by column chromatography on silica gel (eluting with 1% methanol in dichloromethane) to yield 5.7 g of trans-(±) benzyl-3-azido-4-fluoroypyrrolidne-1-carobxylate.

Step 3. Preparation of trans-(±)-Benzyl 3-amino-4-fluoroypyrrolidne-1-carobxylate

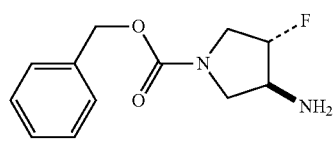

To a solution of trans-(±) benzyl-3-azido-4-fluoroypyrrolidne-1-carobxylate (4.33 g) in tetrahydrofuran (100 mL) and water (10 mL) was added triphenylphospine (4.5 g). The reaction mixture was heated under reflux for 2 hours. The reaction mixture was concentrated in vacuo and the residue was dissolved in ethyl acetate (50 mL). The solution was extracted with 15% aqueous solution of citric acid (30 mL×2) and the aqueous layers were combined, basified with a concentrated aqueous ammonium hydroxide to about pH 9, then extracted with ethyl acetate (50 mL×2). The combined organic layers were washed with brine (50 mL), dried over magnesium sulfate and concentrated in vacuo to afford trans-(±)-benzyl 3-amino-4-fluoroypyrrolidne-1-carobxylate.

The following examples were prepared by the general methods outlined in the schemes above. They are intended to illustrate the meaning of the present invention but should by no means represent a limitation within the meaning of the present invention.

Example 1-1

N-[2-(1,1-Dioxido-2,3-dihydro-1,4-benzothiazepin-4 (5H)-yl)thieno[3,2-d]pyrimidin-4-yl]-2,2-difluoro-propane-1,3-diamine

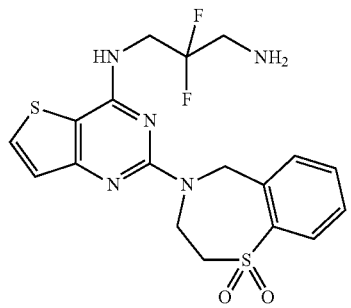 [SMILES: NCC(F)(F)CNc1nc(N2CCS(=O)(=O)c3ccccc3C2)nc2ccsc12]

Step 1. Preparation of N-1-(2-Chlorothieno[3,2-d]pyrimidin-4-yl)-2,2-difluoropropane-1,3-diamine

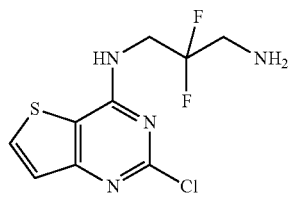 [SMILES: NCC(F)(F)CNc1nc(Cl)nc2ccsc12]

To a mixture of 2,2-difluoropropane-1,3-diamine (1.07 g, 9.6 mmol) in dichloromethane (15 mL) and triethylamine (4 mL, 28.7 mol) was added dropwise a solution of 2,4-dichlorothieno[3,2-d]pyrimidine (0.98 g, 4.8 mmol) in dichloromethane (5 mL). The mixture was stirred at room temperature overnight, then water (50 mL) was added. The mixture was extracted with dichloromethane. The organic phase was washed with brine, dried with anhydrous sodium sulfate, then the solvent was removed and the residue was purified by flash column chromatography (eluting with 10%-30% methanol in dichloromethane) to afford 1.0 g of N-1-(2-chlorothieno[3,2- d]pyrimidin-4-yl)-2,2-difluoropropane-1,3-diamine (yield was 75%). MS obsd. (ESI⁺)[(M+H)⁺]: 279.

Step 2. Preparation of N-[2-(1,1-Dioxido-2,3-dihydro-1,4-benzothiazepin-4(5H)-yl)thieno[3,2-d]pyrimidin-4-yl]-2,2-difluoropropane-1,3-diamine

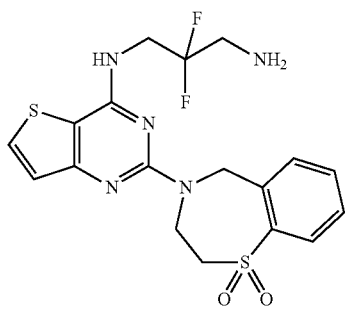 [SMILES: NCC(F)(F)CNc1nc(N2CCS(=O)(=O)c3ccccc3C2)nc2ccsc12]

A mixture of N-1-(2-chlorothieno[3,2-d]pyrimidin-4-yl)-2,2-difluoropropane-1,3-diamine (92 mg, 0.33 mmol), 6,7,8,9-tetrahydro-5-thia-8-aza-benzocycloheptene-5,5-dioxide (340 mg, 1.72 mmol) in n-butanol (1 mL) was heated at 160° C. for 30 min, the crude was purified by preparative HPLC to afford N-[2-(1,1-dioxido-2,3-dihydro-1,4-benzothiazepin-4(5H)-yl)thieno[3,2-d]pyrimidin-4-yl]-2,2-difluoropropane-1,3-diamine as a white solid. MS obsd. (ESI⁺) [(M+H)⁺] 440, ¹H NMR (400 MHz, METHANOL-d4) δ ppm 7.98 (d, J=7.6 Hz, 1H), 7.82 (d, J=7.3 Hz, 1H), 7.78 (d, J=5.3 Hz, 1H), 7.60 (t, J=7.1 Hz, 1H), 7.41-7.49 (m, 1H), 7.10 (d, J=5.3 Hz, 1H), 5.18 (br. s., 2H), 4.52-4.65 (m, 2H), 4.15 (t, J=13.5 Hz, 2H), 3.53 (t, J=5.1 Hz, 2H), 3.04 (t, J=14.3 Hz, 2H).

Example 1-2

N-[2-(1-Oxido-2,3-dihydro-1,4-benzothiazepin-4(5H)-yl)thieno[3,2-d]pyrimidin-4-yl]propane-1,3-diamine

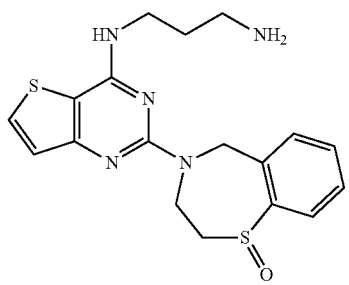 [SMILES: NCCCNc1nc(N2CCS(=O)c3ccccc3C2)nc2ccsc12]

The title compound was prepared in analogy to Example 1-1 in Scheme 1 by using 2,4-dichlorothieno[3,2-d]pyrimidine and propane-1,3-diamine, followed by reaction with 2,3,4,5-tetrahydro-1,4-benzothiazepine-1-oxide. MS obsd. (ESI⁺) [(M+H)⁺] 388, ¹H NMR (400 MHz, METHANOL-d4) δ ppm 7.73-7.78 (m, 2H), 7.71 (d, J=8.3 Hz, 1H), 7.43-7.52 (m, 2H), 7.11 (d, J=5.3 Hz, 1H), 5.24 (d, J=15.2 Hz, 2H), 3.68-3.74 (m, 2H), 3.50 (br. s., 2H), 3.46 (br. s., 2H), 2.93 (t, J=7.6 Hz, 2H), 1.93-2.03 (m, 2H)

Example 1-3

N-[6-Methyl-2-(1,2,3,5-tetrahydro-4H-1,4-benzodiazepin-4-yl)thieno[3,2-d]pyrimidin-4-yl]propane-1,3-diamine

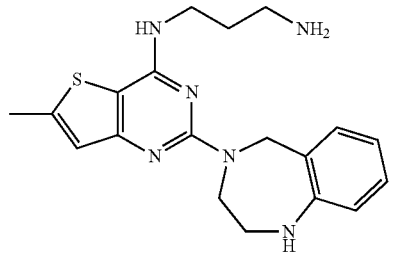 [SMILES: Cc1cc2nc(N3CCNc4ccccc4C3)nc(NCCCN)c2s1]

The title compound was prepared in analogy to Example 1-1 in Scheme 1 by using 2,4-dichloro-6-methylthieno[3,2-d]pyrimidine and propane-1,3-diamine, followed by reaction with 2,3,4,5-tetrahydro-1H-benzo[e][1,4]diazepine. MS obsd. (ESI⁺) [(M+H)⁺] 369, ¹H NMR (400 MHz, METHANOL-d4) δ ppm 7.35 (d, J=7.1 Hz, 1H), 7.00-7.07 (m, 1H), 6.76-6.87 (m, 3H), 4.82 (s, 2H), 4.01-4.06 (m, 2H), 3.70 (t, J=6.6 Hz, 2H), 3.18-3.23 (m, 2H), 2.87 (t, J=6.4 Hz, 2H), 2.54 (s, 3H), 1.91-1.99 (m, 2H).

Example 1-4

N-[2-(1,2,3,5-Tetrahydro-4H-1,4-benzodiazepin-4-yl)thieno[3,2-d]pyrimidin-4-yl]propane-1,3-diamine

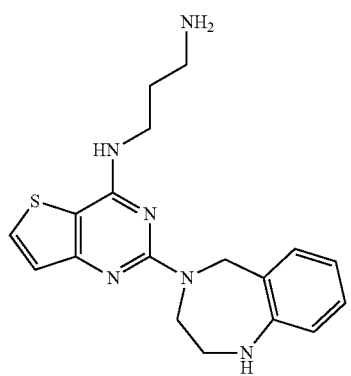 [SMILES: NCCCNc1nc(N2CCNc3ccccc3C2)nc2ccsc12]

The title compound was prepared in analogy to Example 1-1 in Scheme 1 by using 2,4-dichlorothieno[3,2-d]pyrimidine and propane-1,3-diamine, followed by reaction with 2,3,4,5-tetrahydro-1H-benzo[e][1,4]diazepine. MS obsd. (ESI⁺) [(M+H)⁺] 355, ¹H NMR (400 MHz, METHANOL-d4) δ ppm 7.71 (d, J=5.6 Hz, 1H), 7.37 (d, J=7.1 Hz, 1H), 7.08 (d, J=5.3 Hz, 1H), 7.02-7.07 (m, 1H), 6.79-6.86 (m, 2H), 4.85 (s, 2H), 4.04-4.09 (m, 2H), 3.73 (t, J=6.6 Hz, 2H), 3.20-3.24 (m, 2H), 2.86-2.92 (m, 2H), 1.93-2.03 (m, 2H).

Example 1-5

N-[2-(2,3-Dihydro-1,4-benzothiazepin-4(5H)-yl)thieno[3,2-d]pyrimidin-4-yl]propane-1,3-diamine

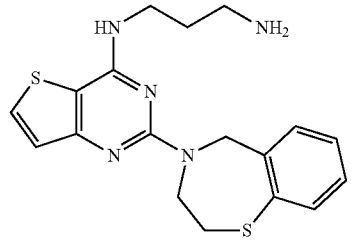 [SMILES: NCCCNc1nc(N2CCSc3ccccc3C2)nc2ccsc12]

The title compound was prepared in analogy to Example 1-1 in Scheme 1 by using 2,4-dichlorothieno[3,2-d]pyrimidine and propane-1,3-diamne) and 6,7,8,9-tetrahydro-5-thia-8-aza-benzocycloheptene. MS obsd. (ESI⁺) [(M+H)⁺] 372, ¹H NMR (400 MHz, METHANOL-d4) δ ppm 7.71 (d, J=5.3 Hz, 1H), 7.65 (d, J=7.1 Hz, 1H), 7.50 (d, J=7.1 Hz, 1H), 7.17-7.25 (m, 1H), 7.10-7.16 (m, 1H), 7.09 (d, J=5.6 Hz, 1H), 5.01 (s, 2H), 4.35 (br. s., 2H), 3.72 (t, J=6.6 Hz, 2H), 2.92-2.96 (m, 2H), 2.87-2.92 (m, 2H), 1.92-2.01 (m, 2H).

Example 1-6

N-[2-(2,3-Dihydro-1,4-benzoxazepin-4(5H)-yl)thieno[3,2-d]pyrimidin-4-yl]propane-1,3-diamine

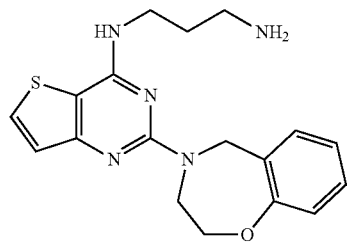 [SMILES: NCCCNc1nc(N2CCOc3ccccc3C2)nc2ccsc12]

The title compound was prepared in analogy to Example 1-1 in Scheme 1 by using 2,4-dichlorothieno[3,2-d]pyrimidine and propane-1,3-diamine, followed by reaction with 2,3,4,5-tetrahydrobenzo[f][1,4]oxazepine. MS obsd. (ESI⁺) [(M+H)⁺] 356, ¹H NMR (400 MHz, METHANOL-d4) δ ppm 7.72 (d, J=5.3 Hz, 1H), 7.43 (d, J=7.1 Hz, 1H), 7.12-7.18 (m, 1H), 7.08 (d, J=5.6 Hz, 1H), 6.93-7.04 (m, 2H), 4.93 (s, 2H), 4.20-4.26 (m, 2H), 4.14-4.19 (m, 2H), 3.71 (t, J=6.4 Hz, 2H), 2.88 (t, J=7.5 Hz, 2H), 1.96 (m, 2H).

Example 1-7

N-[2-(5,5-Difluoro-1,3,4,5-tetrahydro-2H-2-benzazepin-2-yl)thieno[3,2-d]pyrimidin-4-yl]propane-1,3-diamine

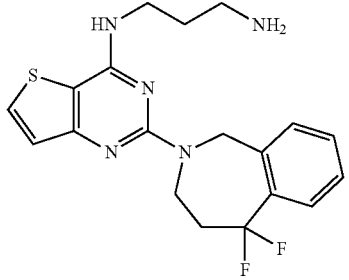 [SMILES: NCCCNc1nc(N2CCC(F)(F)c3ccccc3C2)nc2ccsc12]

The title compound was prepared in analogy to Example-1 in Scheme 1 by using 2,4-dichlorothieno[3,2-d]pyrimidine and propane-1,3-diamne, followed by reaction with 5,5-difluoro-2,3,4,5-tetrahydro-1H-benzo[c]azepine. MS obsd. (ESI⁺) [(M+H)⁺]390, ¹H NMR (400 MHz, METHANOL-d4) δ ppm 7.71 (d, J=5.6 Hz, 1H), 7.60 (d, J=7.8 Hz, 1H), 7.55 (d, J=7.3 Hz, 1H), 7.35-7.41 (m, 1H), 7.27-7.34 (m, 1H), 7.08 (d, J=5.3 Hz, 1H), 4.97 (s, 2H), 4.23-4.31 (m, 2H), 3.70 (t, J=6.6 Hz, 2H), 2.86 (t, J=7.5 Hz, 2H), 2.41-2.53 (m, 2H), 1.94 (m, 2H).

Example 1-8

N-{[3-(Aminomethyl)oxetan-3-yl]methyl}-2-(5,5-difluoro-1,3,4,5-tetrahydro-2H-2-benzazepin-2-yl)thieno[3,2-d]pyrimidin-4-amine

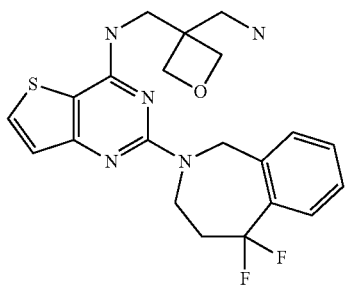 [SMILES: NCC1(CNc2nc(N3CCC(F)(F)c4ccccc4C3)nc3ccsc23)COC1]

The title compound was prepared in analogy to Example 1-1 in Scheme 1 by using 2,4-dichlorothieno[3,2-d]pyrimidine and (3-aminomethyl-oxetan-3-yl)-methylamine, followed by reaction with 5,5-difluoro-2,3,4,5-tetrahydro-1H-benzo[c]azepine. MS obsd. (ESI⁺) [(M+H)⁺] 432, ¹H NMR (400 MHz, METHANOL-d4) δ ppm 7.73 (d, J=5.3 Hz, 1H), 7.60 (d, J=7.8 Hz, 2H), 7.35-7.41 (m, 1H), 7.27-7.34 (m, 1H), 7.09 (d, J=5.3 Hz, 1H), 4.97 (s, 2H), 4.64 (d, J=6.3 Hz, 2H), 4.48 (d, J=6.3 Hz, 2H), 4.24-4.31 (m, 2H), 4.03 (s, 2H), 3.00 (s, 2H), 2.41-2.54 (m, 2H).

Example 1-9

N-[2-(1,3,4,5-Tetrahydro-2H-2-benzazepin-2-yl)thieno[3,2-d]pyrimidin-4-yl]propane-1,3-diamine

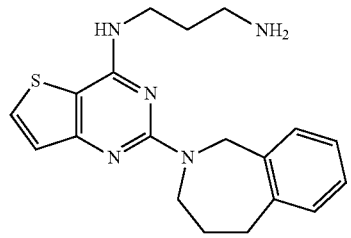 [SMILES: NCCCNc1nc(N2CCCc3ccccc3C2)nc2ccsc12]

The title compound was prepared in analogy to Example 1-1 in Scheme 1 by using 2,4-dichlorothieno[3,2-d]pyrimidine and propane-1,3-diamine, followed by reaction with 2,3,4,5-tetrahydro-1,4-benzothiazepine-1-oxide. MS obsd. (ESI$^+$) [(M+H)$^+$] 354, $^1$H NMR (400 MHz, METHANOL-d4) δ ppm 7.69 (d, J=5.3 Hz, 1H), 7.41-7.45 (m, 1H), 7.06-7.16 (m, 4H), 4.88 (s, 2H), 4.12 (br. s., 2H), 3.73 (t, J=6.6 Hz, 2H), 3.00-3.08 (m, 2H), 2.90 (t, J=7.5 Hz, 2H), 1.94-2.00 (m, 2H), 1.83-1.93 (m, 2H).

Example 1-10

N-[2-(2,3-Dihydro-1,4-benzothiazepin-4(5H)-yl)-6-methylthieno[3,2-d]pyrimidin-4-yl]propane-1,3-diamine

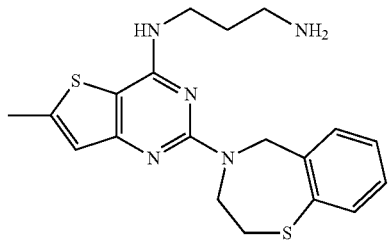 [SMILES: Cc1cc2nc(N3CCSc4ccccc4C3)nc(NCCCN)c2s1]

The title compound was prepared in analogy to Example 1-1 in Scheme 1 by using 2,4-dichloro-6-methylthieno[3,2-d]pyrimidine and propane-1,3-diamne, followed by reaction with 2,3,4,5-tetrahydro-1,4-benzothiazepine. MS obsd. (ESI$^+$) [(M+H)$^+$] 386, $^1$H NMR (400 MHz, METHANOL-d4) δ ppm 7.61-7.71 (m, 1H), 7.53 (d, J=7.6 Hz, 1H), 7.15-7.23 (m, 1H), 7.08-7.15 (m, 1H), 6.80 (s, 1H), 5.00 (s, 2H), 4.41 (br. s., 2H), 3.75 (d, J=4.0 Hz, 2H), 2.89-2.98 (m, 4H), 2.53 (s, 3H), 1.84 (m, 2H).

Example 1-11

N-[2-(2,3-Dihydro-1,4-benzoxazepin-4(5H)-yl)-6-methylthieno[3,2-d]pyrimidin-4-yl]propane-1,3-diamine

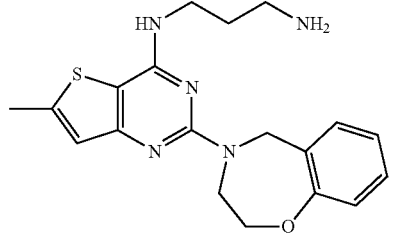 [SMILES: Cc1cc2nc(N3CCOc4ccccc4C3)nc(NCCCN)c2s1]

The title compound was prepared in analogy to Example 1-1 in Scheme 1 by using 2,4-dichloro-6-methylthieno[3,2-d]pyrimidine and propane-1,3-diamine, followed by reaction with 2,3,4,5-tetrahydro-1,4-benzoxazepine. MS obsd. (ESI$^+$) [(M+H)$^+$] 370; $^1$H NMR (400 MHz, METHANOL-d4) δ ppm 7.43 (d, J=6.6 Hz, 1H), 7.10-7.19 (m, 1H), 6.94-7.05 (m, 2H), 6.80 (s, 1H), 4.92 (s, 2H), 4.25-4.32 (m, 2H), 4.14-4.21 (m, 2H), 3.74 (br. s., 2H), 2.96 (t, J=6.3 Hz, 2H), 2.49-2.57 (m, 3H), 1.88 (m, 2H).

Example 1-12

N-[2-(5,5-Difluoro-1,3,4,5-tetrahydro-2H-2-benzazepin-2-yl)-6-methylthieno[3,2-d]pyrimidin-4-yl]propane-1,3-diamine

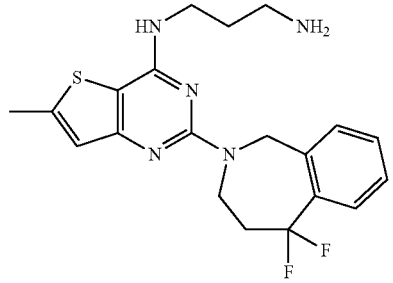 [SMILES: Cc1cc2nc(N3CCC(F)(F)c4ccccc4C3)nc(NCCCN)c2s1]

The title compound was prepared in analogy to Example 1-1 in Scheme 1 by using 2,4-dichlorothieno[3,2-d]pyrimidine and propane-1,3-diamine, followed by reaction with 5,5-difluoro-1,3,4,5-tetrahydro-2H-2-benzazepine. MS obsd. (ESI$^+$) [(M+H)$^+$] 404, $^1$H NMR (400 MHz, METHANOL-d4) δ ppm 7.61 (d, J=7.1 Hz, 1H), 7.50 (d, J=7.1 Hz, 1H), 7.20-7.34 (m, 2H), 6.78 (br, 1H), 4.93 (s, 2H), 4.31 (br, 2H), 3.73 (br. s., 2H), 3.03 (t, J=6.2 Hz, 2H), 2.40-2.56 (m, 3H), 1.97 (m, 2H).

Example 1-13

N-[6-Methyl-2-(1,3,4,5-tetrahydro-2H-2-benzazepin-2-yl)thieno[3,2-d]pyrimidin-4-yl]propane-1,3-diamine

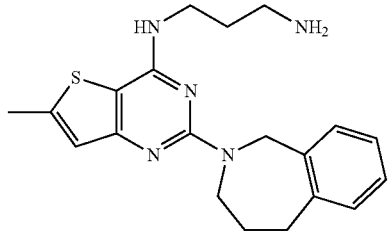 [SMILES: Cc1cc2nc(N3CCCc4ccccc4C3)nc(NCCCN)c2s1]

The title compound was prepared in analogy to Example 1-1 in Scheme 1 by using 2,4-dichlorothieno[3,2-d]pyrimidine and propane-1,3-diamne, followed by reaction with 1,3,4,5-tetrahydro-2H-2-benzazepine. MS obsd. (ESI$^+$) [(M+H)$^+$] 368, $^1$H NMR (400 MHz, METHANOL-d4) δ ppm 7.08-7.15 (m, 4H), 6.88 (br. s., 1H), 4.85 (s, 2H), 4.06-4.18 (m, 2H), 3.70-3.81 (m, 2H), 3.12 (br. s., 2H), 2.94-3.06 (m, 2H), 2.41 (s, 3H), 2.0-2.1 (m, 2H), 1.83-1.93 (m, 2H).

Example 1-14

N-[2-(1,1-Dioxido-2,3-dihydro-1,4-benzothiazepin-4(5H)-yl)-6-methylthieno[3,2-d]pyrimidin-4-yl]propane-1,3-diamine

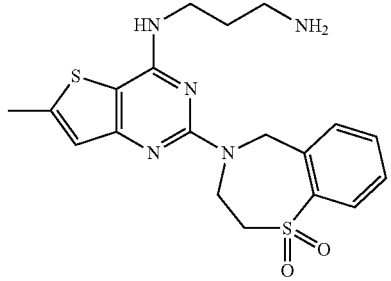 [SMILES: Cc1cc2nc(N3CCS(=O)(=O)c4ccccc4C3)nc(NCCCN)c2s1]

The title compound was prepared in analogy to Example 1 in Scheme 1 by using 2,4-dichlorothieno[3,2-d]pyrimidine and propane-1,3-diamne, followed by reaction with 2,3,4,5-tetrahydro-1,4-benzothiazepine-1,1-dioxide. MS obsd. (ESI$^+$) [(M+H)$^+$] 418, $^1$HNMR (400 MHz, CHLOROFORM-d) δ ppm 8.06 (d, J=7.8 Hz, 1H), 7.49-7.57 (m, 1H), 7.36-7.44 (m, 1H), 7.25-7.30 (m, 1H), 7.02 (s, 1H), 5.20 (m, 2H), 3.98 (br, s, 2H), 3.81 (t, J=6.4 Hz, 2H), 3.74 (br. s., 2H), 3.48 (br. s., 2H), 2.56 (s, 3H), 2.10-2.19 (m, 2H).

Example 1-15

N-[2-(1,1-Dioxido-2,3-dihydro-1,4-benzothiazepin-4(5H)-yl)thieno[3,2-d]pyrimidin-4-yl]propane-1,3-diamine

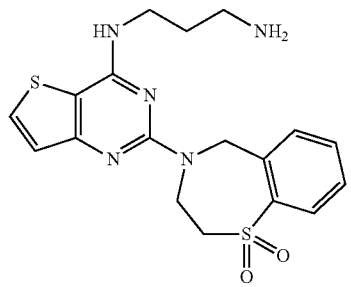 [SMILES: NCCCNc1nc(N2CCS(=O)(=O)c3ccccc3C2)nc2ccsc12]

The title compound was prepared in analogy to Example 1-1 in Scheme 1 by using 2,4-dichlorothieno[3,2-d]pyrimidine and propane-1,3-diamne, followed by reaction with 2,3,4,5-tetrahydro-1,4-benzothiazepine-1,1-dioxide. MS obsd. (ESI$^+$) [(M+H)$^+$] 404, $^1$H NMR (400 MHz, METHANOL-d4) δ ppm 8.04 (d, J=7.3 Hz, 1H), 7.73 (d, J=7.1 Hz, 1H), 7.46-7.57 (m, 2H), 7.34-7.42 (m, 1H), 7.10 (d, J=5.3 Hz, 1H), 5.19 (br. s., 2H), 3.76 (br. s., 2H), 3.44-3.54 (m, 4H), 3.00 (t, J=6.1 Hz, 2H), 1.88 (m, 2H).

Example 2-1 and Example 2-2

N-[(3-Aminooxetan-3-yl)methyl]-2-(1,1-dioxido-2,3-dihydro-1,4-benzothiazepin-4(5H)-yl)thieno[3,2-d]pyrimidin-4-amine and N-[3-(aminomethyl)oxetan-3-yl]-2-(1,1-dioxido-2,3-dihydro-1,4-benzothiazepin-4(5H)-yl)thieno[3,2-d]pyrimidin-4-amine Example 2-1

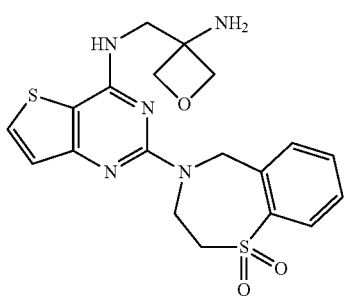

Example 2-2

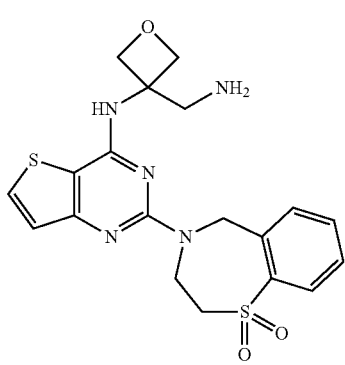

Step 1. Preparation of N-[(3-Aminooxetan-3-yl)methyl]-2-chloro-thieno[3,2-d]pyrimidin-4-amine and N-[3-(aminomethyl)oxetan-3-yl]-2 chlorothieno[3,2-d]pyrimidin-4-amine

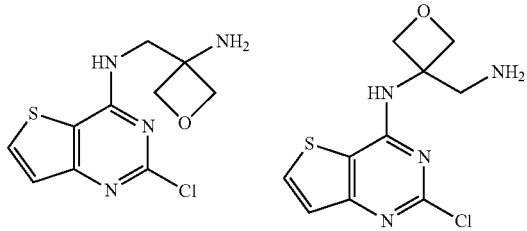 [SMILES: NC1(CNc2nc(Cl)nc3ccsc23)COC1 ; NCC1(Nc2nc(Cl)nc3ccsc23)COC1]

To a mixture of 3-aminomethyloxetan-3-ylamine (0.98 g, 9.6 mmol) in dichloromethane (15 mL) and triethylamine (4 mL, 28.7 mol) was added a solution of 2,4-dichlorothieno[3,2-d]pyrimidine (1.0 g, 4.8 mmol) dropwise in dichloromethane (5 mL). The mixture was stirred at room temperature overnight, then water (50 mL) was added. The mixture was extracted with dichloromethane. The organic phase was washed with brine, dried with anhydrous sodium sulfate. The solvent was then removed and the residue was purified by flash column chromatography (eluting with 10%~30% methanol in dichloromethane) to give 1.0 g of N-[(3-aminooxetan-3-yl)methyl]-2-chlorothieno[3,2-d]pyrimidin-4-amine and N-[3-(aminomethyl)oxetan-3-yl]-2-chlorothieno[3,2-d]pyrimidin-4-amine (yield was 77%). MS obsd. (ESI$^+$) [(M+H)$^+$] 271.

Step 2. Preparation of N-[(3-Aminooxetan-3-yl)methyl]-2-(1,1-dioxido-2,3-dihydro-1,4-benzothiazepin-4(5H)-yl)thieno[3,2-d]pyrimidin-4-amine and N-[3-(aminomethyl)oxetan-3-yl]-2-(1,1-dioxido-2,3-dihydro-1,4-benzothiazepin-4(5H)-yl)thieno[3,2-d]pyrimidin-4-amine

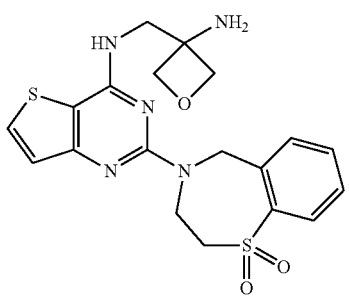 [SMILES: NC1(CNc2nc(N3CCS(=O)(=O)c4ccccc4C3)nc3ccsc23)COC1]

A mixture of N-[(3-aminooxetan-3-yl)methyl]-2-chlorothieno[3,2-d]pyrimidin-4-amine and N-[3-(aminomethyl)oxetan-3-yl]-2-chlorothieno[3,2-d]pyrimidin-4-amine (184 mg, 0.66 mmol), 6,7,8,9-tetrahydro-5-thia-8-aza-benzocycloheptene-5,5-dioxide (680 mg, 3.44 mmol) in n-Butanol (1 mL) was heated at 160° C. for 30 min. The crude was purified by preparative HPLC to afford N-[(3-aminooxetan-3-yl)methyl]-2-(1,1-dioxido-2,3-dihydro-1,4-benzothiazepin-4(5H)-yl)thieno[3,2-d]pyrimidin-4-amine and N-[3-(aminomethyl)oxetan-3-yl]-2-(1,1-dioxido-2,3-dihydro-1,4-benzothiazepin-4(5H)-yl)thieno[3,2-d]pyrimidin-4-amine.

N-[(3-Aminooxetan-3-yl)methyl]-2-(1,1-dioxido-2,3-dihydro-1,4-benzothiazepin-4(5H)-yl)thieno[3,2-d]pyrimidin-4-amine

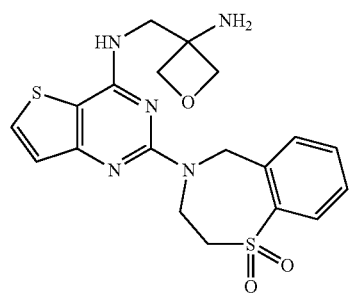

MS obsd. (ESI$^+$) [(M+H)$^+$] 432, $^1$H NMR (400 MHz, METHANOL-d4) δ ppm 7.98 (m, 1H), 7.88 (m, 1H), 7.73 (d, J=5.2 Hz, 1H), 7.59 (m, 1H), 7.425 (m, 1H), 7.07 (d, J=5.6 Hz, 1H), 5.17 (m, 2H), 4.87 (m, 2H), 4.61 (m, 4H), 4.51 (t, J=6.8 Hz, 1H), 4.01 (s, 1H), 3.51 (m, 2H).

N-[3-(Aminomethyl)oxetan-3-yl]-2-(1,1-dioxido-2,3-dihydro-1,4-benzothiazepin-4(5H)-yl)thieno[3,2-d]pyrimidin-4-amine

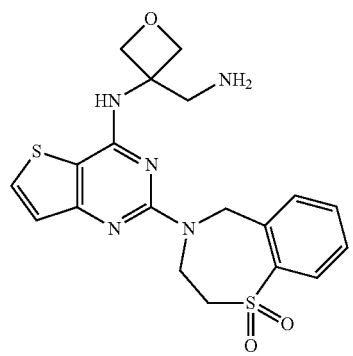 [SMILES: NCC1(Nc2nc(N3CCS(=O)(=O)c4ccccc4C3)nc3ccsc23)COC1]

MS obsd. (ESI$^+$) [(M+H)$^+$] 432, $^1$H NMR (METHANOL-d4) δ ppm 8.03 (d, J=8.0 Hz, 1H), 7.96 (m, 1H), 7.60 (m, 2H), 7.52 (m, 1H), 7.08 (d, J=5.2 Hz, 1H), 5.08 (m, 2H), 4.60 (m, 2H), 4.32 (m, 2H), 4.01-4.16 (m, 2H), 3.73 (m, 4H).

Example 2-3, 2-4

N-[(3-Aminooxetan-3-yl)methyl]-2-[(1R)-1-oxido-2,3-dihydro-1,4-benzothiazepin-4(5H)-yl]thieno[3,2-d]pyrimidin-4-amine and N-[(3-aminooxetan-3-yl)methyl]-2-[(1S)-1-oxido-2,3-dihydro-1,4-benzothiazepin-4(5H)-yl]thieno[3,2-d]pyrimidin-4-amine

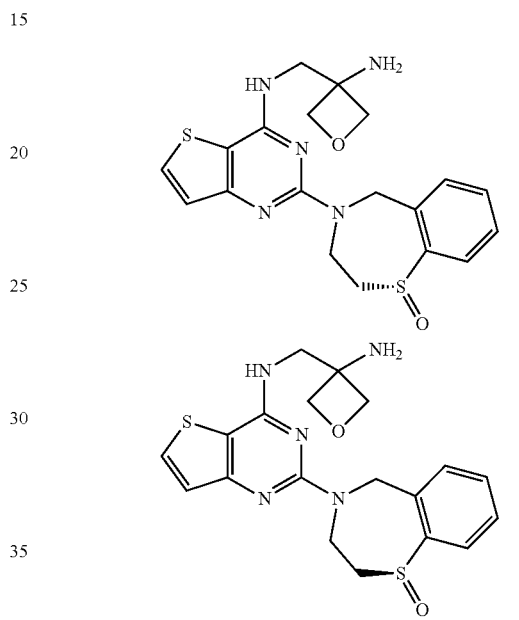

The title racemic compound was prepared in analogy to Example 2-1 in Scheme 2 by using 2,4-dichlorothieno[3,2-d]pyrimidine with 3-aminomethyloxetan-3-ylamine, followed by reaction with 2,3,4,5-tetrahydro-1,4-benzothiazepine-1,1-dioxide.

The chiral separation of racemic compound (column: IA; flow rate: 15 mL/min; gradient: 50% hexane in ethanol with 0.4% of triethylamine) gives:

N-[(3-Aminooxetan-3-yl)methyl]-2-[(1R)-1-oxido-2,3-dihydro-1,4-benzothiazepin-4(5H)-yl]thieno[3,2-d]pyrimidin-4-amine MS obsd. (ESI$^+$) [(M+H)$^+$] 416, $^1$H NMR (400 MHz, METHANOL-d4) δ ppm 8.17 (d, J=5.6 Hz, 1H), 7.78-7.81 (m, 2H), 7.31-7.59 (m, 2H), 7.31 (d, J=5.2 Hz, 1H), 5.39 (d, J=5.2 Hz, 1H), 5.08 (brs, 1H), 4.73-4.79 (m, 5H), 4.31-4.50 (m, 3H), 3.50 (s, 2H)

And N-[(3-Aminooxetan-3-yl)methyl]-2-[(1S)-1-oxido-2,3-dihydro-1,4-benzothiazepin-4(5H)-yl]thieno[3,2-d]pyrimidin-4-amine MS obsd. (ESI$^+$) [(M+H)$^+$] 416, $^1$H NMR (400 MHz, METHANOL-d4) δ ppm 8.17 (d, J=5.6 Hz, 1H), 7.78-7.81

(m, 2H), 7.31-7.59 (m, 2H), 7.31 (d, J=5.2 Hz, 1H), 5.39 (d, J=5.2 Hz, 1H), 5.08 (brs, 1H), 4.73-4.79 (m, 5H), 4.31-4.50 (m, 3H), 3.50 (s, 2H)

Example 3-1

N-[(3-Aminooxetan-3-yl)methyl]-6-methyl-2-(1-oxido-2,3-dihydro-1,4-benzothiazepin-4(5H)-yl)thieno[3,2-d]pyrimidin-4-amine

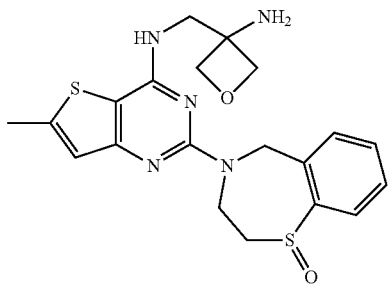 [SMILES: Cc1cc2nc(N3CCS(=O)c4ccccc4C3)nc(NCC3(N)COC3)c2s1]

Step 1. Preparation of 2-Chloro-6-methylthieno[3,2-d]pyrimidin-4(3H)-one

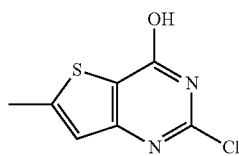

A mixture of 2,4-dichloro-6-methylthieno[3,2-d]pyrimidine (450 mg, 2.05 mmol), aqueous NaOH (1N, 4 mL) and THF (4 mL) was stirred at room temperature under $N_2$. The reaction was monitored by HPLC until the reaction was completed. Then the mixture was neutralized to PH 5 by addition of 2N aqueous HCl. The solid was filtered and dried to give 380 mg of 2-chloro-6-methylthieno[3,2-d]pyrimidin-4(3H)-one (yield was 92%) as a yellow solid. MS obsd. (ESI$^+$) [(M+H)$^+$]: 201.

Step 2. Preparation of 2-(1-Oxido-2,3-dihydro-1,4-benzothiazepin-4(5H)-yl)-6-methylthieno[3,2-d]pyrimidin-4(3H)-one

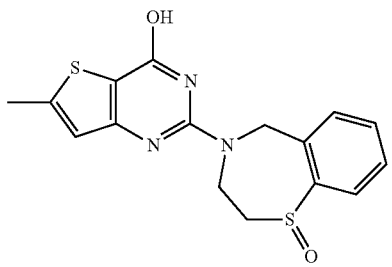 [SMILES: Cc1cc2nc(N3CCS(=O)c4ccccc4C3)nc(O)c2s1]

2-Chloro-6-methylthieno[3,2-d]pyrimidin-4(3H)-one (3.01 g, 15 mmol) was dissolved in toluene (50 mL), followed by addition of 6,7,8,9-tetrahydro-5-thia-8-aza-benzocyclo-heptene-5-oxide (3.39 g, 18.7 mmol), triethylamine (6 mL, 43 mmol). Then the solution was heated to reflux overnight. The suspension was filtrated and the solid was washed by methanol to afford 4.2 g of 2-(1-oxido-2,3-dihydro-1,4-benzothiazepin-4(5H)-yl)-6-methylthieno[3,2-d]pyrimidin-4(3H)-one (yield was 81.1%) as a slight brown solid. MS obsd. (ESI$^+$) [(M+H)$^+$] 346.

Step 3. Preparation of N-[(3-Aminooxetan-3-yl)methyl]-6-methyl-2-(1-oxido-2,3-dihydro-1,4-benzothiazepin-4(5H)-yl)thieno[3,2-d]pyrimidin-4-amine

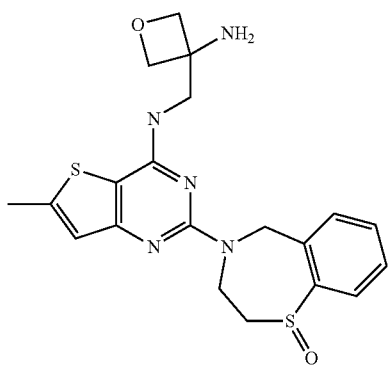 [SMILES: Cc1cc2nc(N3CCS(=O)c4ccccc4C3)nc(NCC3(N)COC3)c2s1]

A suspension of 2-(1-oxido-2,3-dihydro-1,4-benzothiazepin-4(5H)-yl)-6-methylthieno[3,2-d]pyrimidin-4(3H)-one (250 mg, 0.72 mmol), benzotriazol-1-yloxy-tris(dimethylamino)-phosphonium hexafluorophosphate (415 mg, 0.94 mmol) and 1,8-diazabicycloundec-7-ene (165 mg, 1.08 mmol) in anhydrous N,N-dimethylformamide (10 mL) was stirred at r.t. for 10 min, then a solution of 3-aminomethyl-oxetan-3-ylamine (150 mg, 1.44 mmol) in N,N-dimethylformamide (5 mL) was added dropwise. After the addition was complete, the mixture was heated at 60° C. overnight, then it was diluted with water (50 mL), extracted by dichloromethane, washed by brine, dried with anhydrous sodium sulfate. The solvent was removed and the residue was purified by preparative HPLC to afford N-[(3-aminooxetan-3-yl)methyl]-6-methyl-2-(1-oxido-2,3-dihydro-1,4-benzothiazepin-4(5H)-yl)thieno[3,2-d]pyrimidin-4-amine as a white solid. MS obsd. (ESI$^+$) [(M+H)$^+$] 430, $^1$H NMR (400 MHz, METHANOL-d4) δ ppm 7.67-7.80 (m, 2H), 7.45 (t, J=5.8 Hz, 2H), 6.82 (s, 1H), 5.21 (d, J=15.4 Hz, 1H), 4.71 (br. s., 1H), 4.63 (d, J=6.3 Hz, 2H), 4.46-4.56 (m, 2H), 4.01 (s, 2H), 3.30-3.49 (m, 4H), 2.55 (s, 3H).

Example 3-2

2-Fluoro-N-[6-methyl-2-(1-oxido-2,3-dihydro-1,4-benzothiazepin-4(5H)-yl)thieno[3,2-d]pyrimidin-4-yl]propane-1,3-diamine

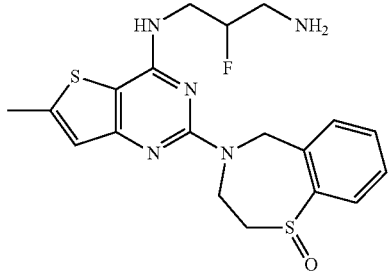 [SMILES: Cc1cc2nc(N3CCS(=O)c4ccccc4C3)nc(NCC(F)CN)c2s1]

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4 (3H)-one and 2-fluoro-1,3-propanediamine. MS obsd. (ESI$^+$) [(M+H)$^+$] 420, $^1$H NMR (400 MHz, METHANOL-d4) δ ppm 7.73 (d, J=6.6 Hz, 1H), 7.68 (d, J=6.8 Hz, 1H), 7.39-7.51 (m, 2H), 6.81 (s, 1H), 5.19 (d, J=14.7 Hz, 1H), 4.83 (d, J=9.3 Hz, 1H), 4.69 (br. s., 2H), 4.46 (br. s., 1H), 3.71-3.96 (m, 2H), 3.30-3.48 (m, 2H), 2.80-3.05 (m, 2H), 2.54 (s, 3H).

Example 3-3

N-[6-Methyl-2-(1-oxido-2,3-dihydro-1,4-benzothiazepin-4(5H)-yl)thieno[3,2-d]pyrimidin-4-yl]ethane-1,2-diamine

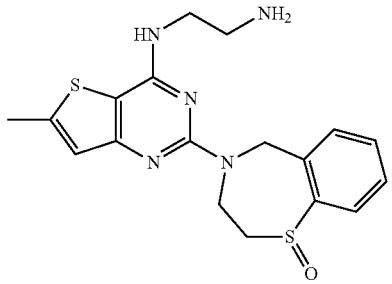 [SMILES: Cc1cc2nc(N3CCS(=O)c4ccccc4C3)nc(NCCN)c2s1]

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4 (3H)-one and ethylenediamine. MS obsd. (ESI$^+$) [(M+H)$^+$] 388, $^1$H NMR (400 MHz, METHANOL-d4) δ ppm 7.68-7.75 (m, 2H), 7.41-7.51 (m, 2H), 6.81 (s, 1H), 5.21 (d, J=5.6 Hz, 1H), 4.65-4.81 (m, 2H), 4.48 (br. s., 1H), 3.68 (m, 2H), 3.32-3.47 (m, 2H), 2.50 (s, 3H).

Example 3-4

N-{[3-(Aminomethyl)oxetan-3-yl]methyl}-6-methyl-2-(1-oxido-2,3-dihydro-1,4-benzothiazepin-4(5H)-yl)thieno[3,2-d]pyrimidin-4-amine

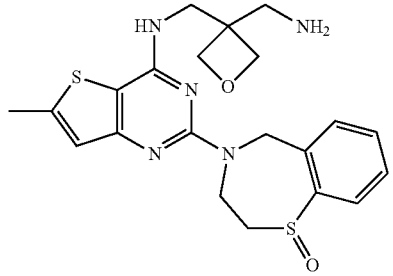 [SMILES: Cc1cc2nc(N3CCS(=O)c4ccccc4C3)nc(NCC3(CN)COC3)c2s1]

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4 (3H)-one and 3,3-oxetanedimethanamine. MS obsd. (ESI$^+$) [(M+H)$^+$] 444, $^1$H NMR (400 MHz, METHANOL-d4) δ ppm 7.74 (t, J=8.7 Hz, 2H), 7.43-7.51 (m, 2H), 6.83 (s, 1H), 5.21 (d, J=15.2 Hz, 1H), 4.68-4.75 (m, 1H), 4.64 (d, J=6.6 Hz, 2H), 4.50 (t, J=6.2 Hz, 2H), 4.01 (br. s., 2H), 3.09 (s, 2H), 2.56 (s, 3H), 2.06 (s, 4H).

Example 3-5

N-[6-Methyl-2-(1-oxido-2,3-dihydro-1,4-benzothiazepin-4(5H)-yl)thieno[3,2-d]pyrimidin-4-yl]propane-1,3-diamine

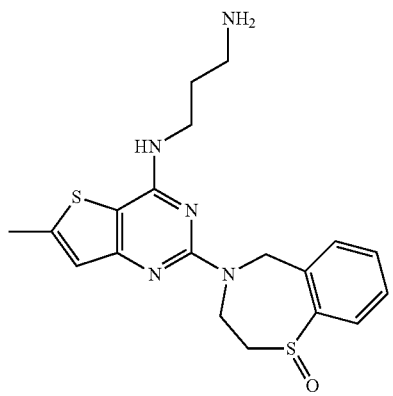 [SMILES: Cc1cc2nc(N3CCS(=O)c4ccccc4C3)nc(NCCCN)c2s1]

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4 (3H)-one and 1,3-propandiamine. MS obsd. (ESI$^+$) [(M+H)$^+$] 402, $^1$H NMR (400 MHz, METHANOL-d4) δ ppm 7.78 (d, J=6.6 Hz, 1H), 7.63 (d, J=7.6 Hz, 1H), 7.34-7.44 (m, 2H), 6.80 (s, 1H), 5.29 (m, 2H), 3.69-3.83 (m, 2H), 3.27-3.42 (m, 2H), 2.97 (t, J=6.3 Hz, 2H), 2.49-2.58 (m, 5H), 1.87 (m, 2H).

Example 4-1

N—[trans-(±)-4-Fluoropyrrolidin-3-yl]-6-methyl-2-(1-oxido-2,3-dihydro-1,4-benzothiazepin-4(5H)-yl)thieno[3,2-d]pyrimidin-4-amine

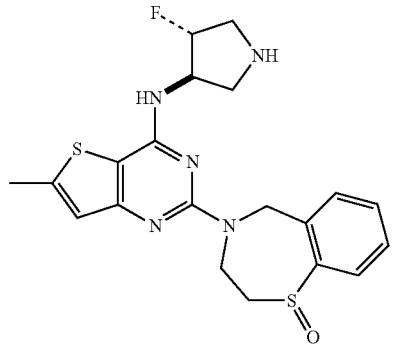

Step 1. Preparation of Benzyl trans-(±)-3-{[2-(1-oxido-2,3-dihydro-1,4-benzothiazepin-4(5H)-yl)-6-methylthineopyrimidin-4-yl]amino}-4-fluoropyrrolidine-1-carboxylate

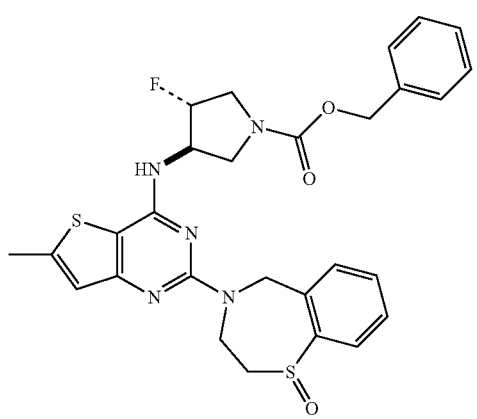

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4 (3H)-one and Benzyl trans-(±)-3-amino-4-fluoro-1-pyrrolidinecarboxylate. MS obsd. (ESI$^+$) [(M+H)$^+$] 566.

Step 2. Preparation of N-[trans-(±)-4-Fluoropyrrolidin-3-yl]-6-methyl-2-(1-oxido-2,3-dihydro-1,4-benzothiazepin-4(5H)-yl)thieno[3,2-d]pyrimidin-4-amine

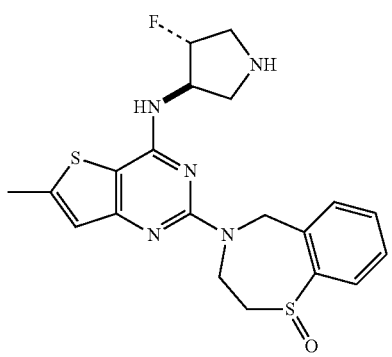

To a suspension of benzyl trans-(±)-3-{[2-(1-oxido-2,3-dihydro-1,4-benzothiazepin-4(5H)-yl)-6-methylthienopyrimidin-4-yl]amino}-4-fluoropyrrolidine-1-carboxylate (320 mg, 0.57 mmol) in methanol (5 mL) was added an aqueous solution of potassium hydroxide (40%, 5 mL). The suspension was heated under reflux for 30 minutes. The organic solvent was removed by concentration in vacuo. The residue was purified by preparative HPLC to afford the pure product as a white solid. MS obsd. (ESI$^+$) [(M+H)$^+$] 432, $^1$H NMR (400 MHz, METHANOL-d4) δ ppm 7.72 (m, 2H), 7.48 (m, 2H), 6.83 (s, 1H), 5.18-5.38 (m, 1H), 4.66-4.99 (m, 5H), 3.26-3.5 (m, 6H), 2.50 (s, 3H).

Example 4-2

6-Methyl-2-(1-oxido-2,3-dihydro-1,4-benzothiazepin-4(5H)-yl)-N-(pyrrolidin-3-yl)thieno[3,2-d]pyrimidin-4-amine

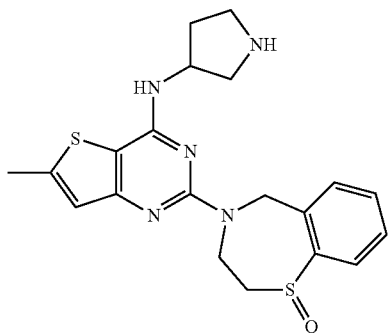 [SMILES: Cc1cc2nc(N3CCS(=O)c4ccccc4C3)nc(NC3CCNC3)c2s1]

Step 1. Preparation of Benzyl 3-{[2-(1-oxido-2,3-dihydro-1,4-benzothiazepin-4(5H)-yl)-6-methylthienopyrimidin-4-yl]amino}-pyrrolidine-1-carboxylate

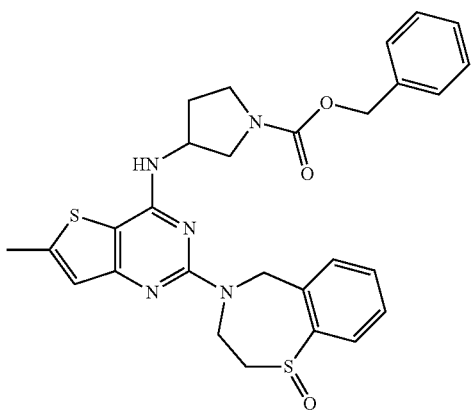 [SMILES: Cc1cc2nc(N3CCS(=O)c4ccccc4C3)nc(NC3CCN(C(=O)OCc4ccccc4)C3)c2s1]

The title compound was prepared in analogy to Example 3-1 in Scheme 3 by using 2-(1-oxido-2,3-dihydro-1,4-benzothiazepin-4(5H)-yl)-6-methylthieno[3,2-d]pyrimidin-4(3H)-one and benzyl-3-amino-1-pyrrolidinecarboxylate. MS obsd. (ESI$^+$) [(M+H)$^+$] 548.

Step 2. Preparation of N-[Pyrrolidin-3-yl]-6-methyl-2-(1-oxido-2,3-dihydro-1,4-benzothiazepin-4(5H)-yl)thieno[3,2-d]pyrimidin-4-amine

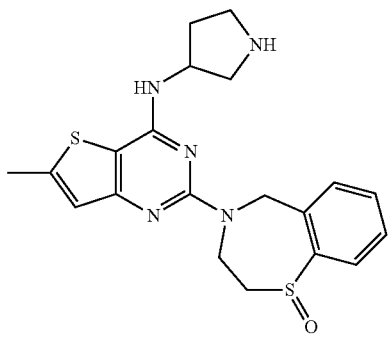 [SMILES: Cc1cc2nc(N3CCS(=O)c4ccccc4C3)nc(NC3CCNC3)c2s1]

To a suspension of benzyl-3-{[2-(1-oxido-2,3-dihydro-1,4-benzothiazepin-4(5H)-yl)-6-methylthienopyrimidin-4-yl]amino}-pyrrolidine-1-carboxylate (300 mg, 0.55 mmol) in methanol (5 mL) was added an aqueous solution of potassium hydroxide (40%, 5 mL). The suspension was heated under reflux for 30 minutes. The organic solvent was removed by concentration in vacuo. The residue was purified by preparative HPLC to afford the pure product as a white solid. MS obsd. (ESI$^+$) [(M+H)$^+$] 414, $^1$H NMR (METHANOL-d4) δ ppm 7.73 (d, J=7.6 Hz, 1H), 7.68 (d, J=7.1 Hz, 1H), 7.37-7.52 (m, 2H), 6.77-6.85 (m, 1H), 5.19 (d, J=15.4 Hz, 1H), 4.79-4.97 (m, 3H), 4.71 (br. s., 1H), 3.44 (d, J=3.0 Hz, 2H), 3.25-3.38 (m, 2H), 3.21 (d, J=5.8 Hz, 1H), 3.02-3.13 (m, 1H), 2.54 (s, 3H), 2.34 (td, J=12.9, 6.9 Hz, 1H), 1.95-2.07 (m, 1H).

Example 5

Viral cytopathic effect (CPE) assay: To measure anti-RSV activity of compounds, 96-well plates are seeded with 6×10$^3$ cells per well in Dulbecco's modified Eagle's medium (DMEM) containing 10% fetal bovine serum (FBS). Cells are infected the next day with sufficient RSV Long strain (ATCC, catalog number: VR-26) to produce an approximately 80-90% cytopathic effect after 6 days, in the presence of serial half-log diluted compound in a total volume of 200 μL per well. The viability of cells is assessed after 6 days using Cell Counting kit-8 (Dojindo Molecular Technologies). The absorbance at 450 nm and referenced at 630 nm is measured to determine 50% effective concentration (EC$_{50}$).

The compounds of the present invention were tested for their anti-RSV activity, and the activation as described herein. The Examples were tested in the above assay and found to have EC$_{50}$ of about 0.0001 μM to about 10 μM. Particular compound of formula (I) were found to have EC$_{50}$ of about 0.0001 μM to about 1 μM. Further particular compound of formula (I) were found to have EC$_{50}$ of about 0.0001 μM to about 0.1 μM.

Results of CPE assays are given in Table 1.

TABLE 1

| Example | EC$_{50}$ (μM, Long Strain) |
|---|---|
| 1-1 | 0.215 |
| 1-2 | 0.255 |
| 1-3 | 3.12 |
| 1-4 | 9.47 |
| 1-5 | 0.384 |
| 1-6 | 2.211 |
| 1-7 | 0.669 |
| 1-8 | 0.022 |
| 1-9 | 0.667 |
| 1-10 | 0.735 |
| 1-11 | 1.353 |
| 1-12 | 1.014 |
| 1-13 | 1.437 |
| 1-14 | 0.073 |
| 1-15 | 0.076 |
| 2-1 | 0.007 |
| 2-2 | 0.897 |
| 2-3 | 0.068 |
| 2-4 | 0.003 |
| 3-1 | 0.026 |
| 3-2 | 0.468 |
| 3-3 | 0.086 |
| 3-4 | 0.006 |
| 3-5 | 0.232 |
| 4-1 | 0.03 |
| 4-2 | 0.676 |

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

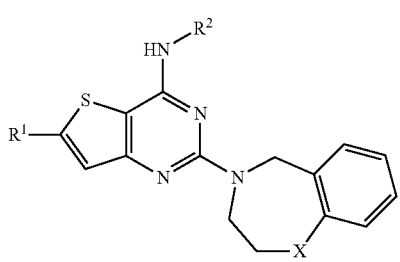

(I)

or a pharmaceutically acceptable salt or stereoisomer thereof, wherein:

$R^1$ is hydrogen or a $C_{1-6}$alkyl;

$R^2$ is (1) amino($CH_2$)$_{2-6}$; (2) amino($CH_2$)$_{1-6}$difluoromethyl($CH_2$)$_{1-6}$; (3) amino($CH_2$)$_{1-6}$fluoromethyl($CH_2$)$_{1-6}$; (4) amino($CH_2$)$_{0-6}$oxetanyl($CH_2$)$_{1-6}$; (5) amino($CH_2$)$_{1-6}$oxetanyl($CH_2$)$_{0-6}$; or (6) pyrrolidin-3-yl, unsubstituted or 4-substituted by halogen; and X is —O—, —S—, —S(=O)—, —S(O$_2$)—, —CH$_2$—, —CF$_2$— or —NH—.

2. A compound according to claim 1 or a pharmaceutically acceptable salt thereof, wherein:

$R^1$ is hydrogen or methyl;

$R^2$ is

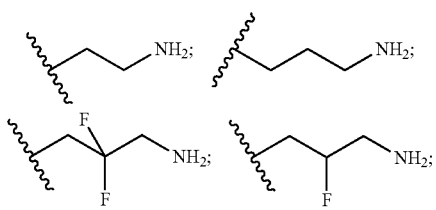

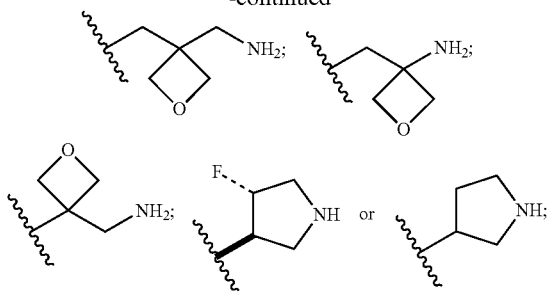

and

X is —O—, —S—, —S(=O)—, —S(O$_2$)—, —CH$_2$—, —CF$_2$— or —NH—.

3. A compound according to claim 2, wherein $R^2$ is

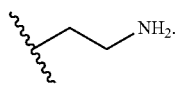

4. A compound according to claim 2, wherein $R^2$ is

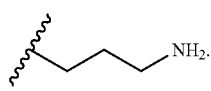 [SMILES: *CCCN]

5. A compound according to claim 2, wherein $R^2$ is

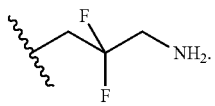 [SMILES: *CC(F)(F)CN]

6. A compound according to claim 2, wherein $R^2$ is

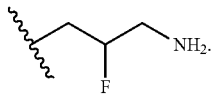 [SMILES: *CC(F)CN]

7. A compound according to claim 2, wherein $R^2$ is

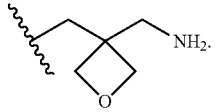 [SMILES: *CC1(CN)COC1]

8. A compound according to claim 2, wherein $R^2$ is

9. A compound according to claim 2, wherein $R^2$ is

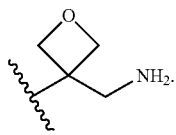 [SMILES: *C1(CN)COC1]

10. A compound according to claim 2, wherein $R^2$ is

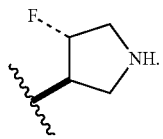

11. A compound according to claim 2, wherein $R^2$ is

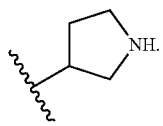 [SMILES: *C1CCNC1]

12. A compound according to claim 1, wherein X is —S—, —S(=O)— or —S(O$_2$)—.
13. A compound according to claim 2, wherein X is —S—.
14. A compound according to claim 2, wherein X is —S(=O)—.
15. A compound according to claim 2, wherein X is —S(O$_2$)—.
16. A compound according to claim 1, wherein:
   $R^1$ is hydrogen or methyl;
   $R^2$ is aminopropyl; aminomethyldifluoromethylmethyl; aminomethyloxetanyl or aminooxetanylmethyl; and
   X is —S—, —S(=O)— or —S(O$_2$)—.
17. A compound according to claim 1, selected from the group consisting of:
   N-[2-(1,1-dioxido-2,3-dihydro-1,4-benzothiazepin-4 (5H)-yl)thieno[3,2-d]pyrimidin-4-yl]-2,2-difluoropropane-1,3-diamine;
   N-[2-(1-oxido-2,3-dihydro-1,4-benzothiazepin-4(5H)-yl) thieno[3,2-d]pyrimidin-4-yl]propane-1,3-diamine;
   N-[2-(2,3-dihydro-1,4-benzothiazepin-4(5H)-yl)thieno[3, 2-d]pyrimidin-4-yl]propane-1,3-diamine;
   N-[2-(2,3-dihydro-1,4-benzothiazepin-4(5H)-yl)-6-methylthieno[3,2-d]pyrimidin-4-yl]propane-1,3-diamine;
   N-[2-(1,1-dioxido-2,3-dihydro-1,4-benzothiazepin-4 (5H)-yl)-6-methylthieno[3,2-d]pyrimidin-4-yl]propane-1,3-diamine;
   N-[2-(1,1-dioxido-2,3-dihydro-1,4-benzothiazepin-4 (5H)-yl)thieno[3,2-d]pyrimidin-4-yl]propane-1,3-diamine;
   N-[(3-aminooxetan-3-yl)methyl]-2-(1,1-dioxido-2,3-dihydro-1,4-benzothiazepin-4(5H)-yl)thieno[3,2-d]pyrimidin-4-amine;
   N-[3-(aminomethyl)oxetan-3-yl]-2-(1,1-dioxido-2,3-dihydro-1,4-benzothiazepin-4(5H)-yl)thieno[3,2-d]pyrimidin-4-amine; and
   N-[(3-aminooxetan-3-yl)methyl]-2-[(1R)-1-oxido-2,3-dihydro-1,4-benzothiazepin-4(5H)-yl]thieno[3,2-d]pyrimidin-4-amine;
or a pharmaceutically acceptable salt thereof.

18. A compound according to claim 1, selected from the group consisting of:
   N-[(3-aminooxetan-3-yl)methyl]-2-[(1S)-1-oxido-2,3-dihydro-1,4-benzothiazepin-4(5H)-yl]thieno[3,2-d]pyrimidin-4-amine;
   N-[(3-aminooxetan-3-yl)methyl]-6-methyl-2-(1-oxido-2, 3-dihydro-1,4-benzothiazepin-4(5H)-yl)thieno[3,2-d] pyrimidin-4-amine;
   2-fluoro-N-[6-methyl-2-(1-oxido-2,3-dihydro-1,4-benzothiazepin-4(5H)-yl)thieno[3,2-d]pyrimidin-4-yl]propane-1,3-diamine;
   N-[6-methyl-2-(1-oxido-2,3-dihydro-1,4-benzothiazepin-4(5H)-yl)thieno[3,2-d]pyrimidin-4-yl]ethane-1,2-diamine;
   N-{[3-(aminomethyl)oxetan-3-yl]methyl}-6-methyl-2-(1-oxido-2,3-dihydro-1,4-benzothiazepin-4(5H)-yl) thieno[3,2-d]pyrimidin-4-amine;
   N-[6-methyl-2-(1-oxido-2,3-dihydro-1,4-benzothiazepin-4(5H)-yl)thieno[3,2-d]pyrimidin-4-yl]propane-1,3-diamine;
   N-[trans-(±)-4-fluoropyrrolidin-3-yl]-6-methyl-2-(1-oxido-2,3-dihydro-1,4-benzothiazepin-4(5H)-yl)thieno [3,2-d]pyrimidin-4-amine;
   6-methyl-2-(1-oxido-2,3-dihydro-1,4-benzothiazepin-4 (5H)-yl)-N-(pyrrolidin-3-yl)thieno[3,2-d]pyrimidin-4-amine; and
   N-[6-methyl-2-(1,2,3,5-tetrahydro-4H-1,4-benzodiazepin-4-yl)thieno[3,2-d]pyrimidin-4-yl]propane-1,3-diamine;
or a pharmaceutically acceptable salt thereof.

19. A compound according to claim 1, selected from the group consisting of:
   N-[2-(1,2,3,5-tetrahydro-4H-1,4-benzodiazepin-4-yl) thieno[3,2-d]pyrimidin-4-yl]propane-1,3-diamine;
   N-[2-(2,3-dihydro-1,4-benzoxazepin-4(5H)-yl)thieno[3, 2-d]pyrimidin-4-yl]propane-1,3-diamine;
   N-[2-(5,5-difluoro-1,3,4,5-tetrahydro-2H-2-benzazepin-2-yl)thieno[3,2-d]pyrimidin-4-yl]propane-1,3-diamine;
   N-{[3-(aminomethyl)oxetan-3-yl]methyl}-2-(5,5-difluoro-1,3,4,5-tetrahydro-2H-2-benzazepin-2-yl)thieno [3,2-d]pyrimidin-4-amine;
   N-[2-(1,3,4,5-tetrahydro-2H-2-benzazepin-2-yl)thieno[3, 2-d]pyrimidin-4-yl]propane-1,3-diamine;
   N-[2-(2,3-dihydro-1,4-benzoxazepin-4(5H)-yl)-6-methylthieno[3,2-d]pyrimidin-4-yl]propane-1,3-diamine;
   N-[2-(5,5-difluoro-1,3,4,5-tetrahydro-2H-2-benzazepin-2-yl)-6-methylthieno[3,2-d]pyrimidin-4-yl]propane-1, 3-diamine; and
   N-[6-methyl-2-(1,3,4,5-tetrahydro-2H-2-benzazepin-2-yl)thieno[3,2-d]pyrimidin-4-yl]propane-1,3-diamine;
or a pharmaceutically acceptable salt thereof.

20. A pharmaceutical composition comprising a compound of claim 1 and a pharmaceutically acceptable excipient.

* * * * *